US 7,432,286 B1

(12) United States Patent
Arkinstall et al.

(10) Patent No.: US 7,432,286 B1
(45) Date of Patent: Oct. 7, 2008

(54) PHARMACEUTICALLY ACTIVE SULFONYL HYDRAZIDE DERIVATIVES

(75) Inventors: Stephen Arkinstall, Belmont, MA (US); Serge Halazy, Vetraz-Monthoux (FR); Dennis Church, Commugny (CH); Montserrat Camps, Versoix (CH); Thomas Rueckle, Plan-les-Ouates (CH); Jean-Pierre Gotteland, Beaumont (FR); Marco Biamonte, San Diego, CA (US)

(73) Assignee: Laboratories Serono SA, Vaud (CH)

( * ) Notice: Subject to any disclaimer, the term of this patent is extended or adjusted under 35 U.S.C. 154(b) by 601 days.

(21) Appl. No.: 10/088,074

(22) PCT Filed: Sep. 28, 2000

(86) PCT No.: PCT/IB00/01381

§ 371 (c)(1),
(2), (4) Date: Oct. 13, 2004

(87) PCT Pub. No.: WO01/23382

PCT Pub. Date: Apr. 5, 2001

(30) Foreign Application Priority Data

Sep. 28, 1999 (EP) .................................. 99810870

(51) Int. Cl.
*C07D 417/12* (2006.01)
*C07D 213/74* (2006.01)
*A61K 31/44* (2006.01)

(52) U.S. Cl. ..................... 514/336; 514/614; 546/268.1; 564/81

(58) Field of Classification Search ............. 546/279.17; 514/336
See application file for complete search history.

(56) References Cited

FOREIGN PATENT DOCUMENTS

| EP | 0 330 065 | 8/1989 |
|---|---|---|
| WO | 98 49188 | 11/1998 |
| WO | WO 01/23378 | 4/2001 |

OTHER PUBLICATIONS

R. Raja Reddy et al.: "New hypoglycemic agents-Part XVI: synthesis and evaluation of N3-aryl-N1-'4-'(3, 4-dihydro-3-oxo-2H-1, 4-benzoxazin-2-yl) acetic acid hydrazidosulfonyllphenyll ureas/thioureas" Indian Journal of Heterocyclic Chemistry, vol. 7, No. 3, pp. 185-188.

Xie Xiaoling et al.: "Crystal structure of JNK3: a kinase implicated in neuronal apoptosis" Structure, 6 (8), pp. 983-991, 1998.

Derek D. Yang et al.: "Absence of excitotoxicity-induced apoptosis in the hippocampus of mice lacking the Jnk3 gene" Nature, 389 (6653), pp. 865-870, 1997.

Derek D. Yang et al.: "Differentiation of CD4+ T cells to Th1 cells requires MAP kinase JNK2" Immunity, 9, pp. 575-585, 1998.

Kanaga Sabapathy et al.: "JNK2 is required for efficient T-cell activation and apoptosis but not for normal lymphocyte development" Current Biology, 3, pp. 116-125, 1999.

Yoshihiro Kumage et al.: "Human c-Jun N-terminal kinase expression and activation in the nervous system" Brain Res. Mol. Brain Res., 67 (1), pp. 10-17, 1999.

*Primary Examiner*—Zinna N Davis
(74) *Attorney, Agent, or Firm*—Oblon, Spivak, McClelland, Maier & Neustadt, P.C.

(57) ABSTRACT

The present invention is related to sulfonyl hydrazide derivatives for use as pharmaceutically active compounds, as well as to pharmaceutical formulations containing such sulfonyl hydrazide derivatives. Said sulfonyl hydrazide derivatives are efficient modulators of the JNK pathway, they are in particular efficient inhibitors of JNK 2 and 3. The present invention is furthermore related to novel sulfonyl hydrazide derivatives as well as to methods of their preparation. In Formula (I) $Ar^1$ and $Ar^2$ are independently from each other an unsubstituted or substituted aryl or beteroaryl group, $X^1$ and $X^2$ are independently from each other O or S; $R^1$, $R^2$, $R^3$ are independently from each other hydrogen or a $C_1$-$C_6$-alkyl substituent or $R^1$ forms a substituted or unsubstituted 5-6-membered saturated or unsaturated ring with $Ar^1$; or $R^2$ and $R^3$ form a substituted or unsubstituted 5-6-membered saturated or unsaturated ring; n is an integer from 0 to 5; G is selected from a group comprising or consisting of an unsubstituted or substituted 4-8 membered heterocycle containing at least one heteroatom, or G is a substituted or unstibstituted $C_1$-$C_6$-alkyl group.

$$Ar^1 \underset{\underset{X^1}{|}}{\overset{\overset{}{|}}{-}} N \underset{\underset{R^1}{|}}{-} (CH_2)_n - Ar^2 - SO_2 - N \underset{\underset{R^2}{|}}{-} N \underset{\underset{X^2}{|}}{\overset{\overset{R^3}{|}}{-}} G \quad (I)$$

33 Claims, No Drawings

PHARMACEUTICALLY ACTIVE SULFONYL HYDRAZIDE DERIVATIVES

CONTINUING DATA

This application is a 371 of PCT/IB00/01381 filed Sep. 28, 2000.

FIELD OF THE INVENTION

The present invention is related to sulfonyl hydrazide derivatives notably for use as pharmaceutically active compounds, as well as pharmaceutical formulations containing such sulfonyl hydrazide derivatives. In particular, the present invention is related to sulfonyl hydrazide derivatives displaying a substantial modulatory, notably inhibitory activity of the JNK (Jun-Kinase) function or pathways respectively, and which are therefore particularly useful in the treatment and/or prevention of disorders of the autoimmune and the neuronal system. The present invention is furthermore related to novel sulfonyl hydrazide derivatives as well as to methods of their preparation.

BACKGROUND OF THE INVENTION

Apoptosis denotes the complex contortions of the membrane and organelles of a cell as it undergoes the process of programmed cell death. During said process, the cell activates an intrinsic suicide program and systematically destroys itself. The following series of events can be observed:

The cell surface begins to bleb and expresses pro-phagocytic signals. The whole apoptotic cell then fragments into membrane-bound vesicles that are rapidly and neatly disposed of by phagocytosis, so that there is minimal damage to the surrounding tissue.

The cell then separates from its neighbors.

The nucleus also goes through a characteristic pattern of morphological changes as it commits genetic suicide, the chromatin condenses and is specifically cleaved to fragments of DNA.

Neuronal cell death plays an important role in ensuring that the nervous system develops normally. It appears that the death of developing neurones depends on the size of the target that they innervate: cells with fewer synaptic partners are more likely to die than those that have formed multiple synapses. This may reflect a process, which balances the relative number of pre- to postsynaptic neurones in the developing nervous system. Although neuronal cell death was assumed to be apoptotic, it was only recently that neurones in developing rodent brain were conclusively shown to undergo apoptosis as classified by morphology and DNA fragmentation. As cell death during development is clearly not a pathological process, it makes sense that cells actually cease to exist.

Neuronal death occurs via either apoptotic or necrotic processes following traumatic nerve injury or during neurodegenerative diseases. Multiple components are emerging as key players having a role in driving neuronal programmed cell death. Amongst the components leading to neuronal apoptosis are members of the SAPK/JNK being a subfamily of MAP Kinases (MAPKs).

MAPKs (mitogen-activated protein kinases) are serine/threonine kinases that are activated by dual phosphorylation on threonine and tyrosine residues. In mammalian cells, there are at least three separate but parallel pathways that convey information generated by extracellular stimuli to the MAPKs. Said pathways consist of kinase cascades leading to activation of the ERKs (extracellular regulated kinases), the JNKs (c-Jun N-terminal kinases), and the p38/CSBP kinases. While both the JNK and p38 pathways are involved in relaying stress-type extramolecular signals, the ERK pathway is primarily responsible for trans-ducing mitogenic/differentiation signals to the cell nucleus.

SAPK cascades represent a sub-family of the mitogen-activating protein kinase family, that are activated by different external stimuli including DNA damage following UV irradiation, TNF-α, IL-1β, ceramide, cellular stress, and reactive oxygen species and have distinct substrate specificities. Signal transduction via MKK4/JNK of MKK3/p38 results in the phosphorylation of inducible transcription factors, c-Jun and ATF2, which then act as either homodimers or heterodimers to initiate transcription of down-stream effectors. c-Jun is a protein that is forming homodimers and heterodimers (with e.g. c-Fos) to produce the transactivating complex AP-which is required for the activation of many genes (e.g. matrix metalloproteinases) involved in the inflammatory response. The JNKs were discovered when it was found that several different stimuli such as UV light and TNF-α stimulated phosphorylation of c-Jun on specific serine residues in the N-terminus of the protein.

In a recent publication of Xie X et al, (*Structure* 1998, 6 (8); 983-991) it has been suggested that activation of stress-activated signal transduction pathways are required for neuronal apoptosis induced by NGF withdrawal in rat PC-12 and superior cervical ganglia (SCG) sympathetic neuronal cells. Inhibition of specific kinases, namely MAP kinase kinase 3 (MKK3) and MAP kinase kinase 4 (MKK4), or c-Jun (part of the MKK-4 cascade) may be sufficient to block apoptosis (see also Kumagae Y et al, in Brain Res Mol Brain Res, 1999, 67(1), 10-17 and Yang D D et al in *Nature*, 1997, 389 (6653); 865-870). Within a few hours of NGF deprivation in SCG neurones, c-Jun becomes highly phosphorylated and protein levels increase. Similarly in rat PC-12 cells deprived of NGF, JNK and p38 undergo sustained activation while ERKs are inhibited. Consistent with this JNK3 KO mice are resistant to excitotoxicity induced apoptosis in the hippocampus and more importantly they display greatly reduced epileptic like seizures in response to excitotoxicity as compared to normal animals (*Nature* 1997, 389, 865-870).

More recently, it has been reported that the JNK signalling pathway is implicated in cell proliferation and could play an important role in autoimmune diseases (*Immunity*, 1998, 9, 575-585; *Current Biology*, 1999, 3, 116-125) which are mediated by T-cell activation and proliferation.

Naive (precursor) CD4+ helper T (Th) cells recognise specific MHC-peptide complexes on antigen-presenting cells (APC) via the T-cell receptor (TCR) complex. In addition to the TCT-mediated signal, a costimulatory signal is provided at least partially by the ligation of CD28 expressed on T-cells with B7 proteins on APC. The combination of these two signals induces T-cell clonal expression.

After 4-5 days of proliferation, precursor of CD4+ T cells differentiate into armed effector Th cells that mediate the functions of the immune system. During the differentiation process, substantial reprogramming of gene expression occurs.

Two subsets of effector Th cells have been defined on the basis of their distinct cytokine secretion pattern and their immunomodulatory effects: Th1 cells produce IFNγ and LT (TNF-β), which are required for cell-mediated inflammatory reactions; Th2 cells secrete IL-4, IL-5, IL-6, IL-10 and IL-13, which mediate B cell activation and differentiation. These cells play a central role in the immune response. The JNK MAP Kinase pathway is induced in Th1 but not in Th2 effector cells upon antigen stimulation. Furthermore, the differentiation of precursor CD4+ T cells into effector Th1 but not Th2 cells is impaired in JNK2-deficient mice. Therefore, in recent years it has been realized that the JNK kinase pathway plays an important role in the balance of Th1 and Th2 immune response through JNK2.

With the objective of inhibiting the JNK kinase pathway, WO/9849188 teaches the use of a human polypeptide, i.e. JNK-interacting protein 1 (JIP-1), which is a biological product and which has also been assayed for overcoming apoptosis related disorders.

Active bio-peptides or bio-proteins are only obtained by means of rather comprehensive and expensive bio-synthesis which consequently frequently renders the resulting products fairly cost-intensive.

The peptides are known to display poor membrane penetration and may not cross the blood brain membrane, The principal drawback to the use of peptide inhibitors or antagonists is the problem of low oral bioavailability resulting from intestinal degradation. Hence, they must be administered parenterally and finally, peptide inhibitors or antagonists are frequently viewed by the host body as intruding material to be eliminated, thus setting off an auto-immune response.

Hence, it is an objective of the present invention to provide relatively small molecules that avoid essentially all of the above-mentioned drawbacks arising from the use of peptides or proteins, however, which are suitable for the treatment of a variety of diseases, in particular of neuronal or the autoimmune system related disorders. It is notably an objective of the present invention to provide relatively small molecule chemical compounds which are able to modulate, preferably to down-regulate or to inhibit the JNK (Jun kinase) pathway so to be available as a convenient method of treating diseases which are preferably mediated by the JNK function. Moreover, it is an objective of the present invention to provide methods for preparing said small molecule chemical compounds. It is furthermore an objective of the present invention to provide a new category of pharmaceutical formulations for the treatment of diseases, preferably mediated by the JNK function. It is finally an objective of the present invention to provide a method for the treatment and/or prevention of diseases that are caused by disorders of the autoimmune and/or the neuronal system.

DESCRIPTION OF THE INVENTION

The aforementioned objectives have been met according to the independent claims. Pre-ferred embodiments are set out within the dependent claims.

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to monovalent alkyl groups having 1 to 6 carbon atoms. This term is exemplified by groups such as methyl, ethyl, n-propyl, isopropyl, n-butyl, isobutyl, tertbutyl, n-hexyl and the like.

"Aryl" refers to an unsaturated aromatic carbocyclic group of from 6 to 14 carbon atoms having a single ring (e.g. phenyl) or multiple condensed rings (e.g. naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetra-hydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"Alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"Alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"Acyl" refers to the group —C(O)R where R includes "$C_1$-$C_6$-alkyl", "aryl", "heteroaryl", "$C_1$-$C_6$-alkyl aryl" or "$C_1$-$C_6$-alkyl heteroaryl".

"Acyloxy" refers to the group —OC(O)R where R includes "$C_1$-$C_6$-alkyl", "aryl", "heteroaryl", "$C_1$-$C_6$-alkyl aryl" or "$C_1$-$C_6$-alkyl heteroaryl".

"Alkoxy" refers to the group —O—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred alkoxy groups include by way of example, methoxy, ethoxy, phenoxy and the like.

"Alkoxycarbonyl" refers to the group —C(O)OR where R includes "$C_1$-$C_6$-alkyl" or "aryl" or "heteroaryl" or "$C_1$-$C_6$-alkyl aryl" or "$C_1$-$C_6$-alkyl heteroaryl".

"Aminocarbonyl" refers to the group —C(O)NRR' where each R, R' includes independently hydrogen or $C_1$-$C_6$-alkyl or aryl or heteroaryl or "$C_1$-$C_6$-alkyl aryl" or "$C_1$-$C_6$-alkyl heteroaryl".

"Acylamino" refers to the group —NR(CO)R' where each R, R' is independently hydrogen or "$C_1$-$C_6$-alkyl" or "aryl" or "heteroaryl" or "$C_1$-$C_6$-alkyl aryl" or "$C_1$-$C_6$-alkyl heteroaryl".

"Halogen" refers to fluoro, chloro, bromo and iodo atoms.

"Sulfonyl" refers to group "—$SO_2$—R" wherein R is selected from H, "aryl", "heteroaryl", "$C_1$-$C_6$-alkyl", "$C_1$-$C_6$-alkyl" substituted with halogens e.g. an —$SO_2$—$CF_3$ group, "$C_1$-$C_6$-alkyl aryl" or "$C_1$-$C_6$-alkyl heteroaryl".

"Sulfoxy" refers to a group "—S(O)—R" wherein R is selected from H, "$C_1$-$C_6$-alkyl", "$C_1$-$C_6$-alkyl" substituted with halogens e.g. an —SO—$CF_3$ group, "aryl", "heteroaryl", "$C_1$-$C_6$-alkyl aryl" or "$C_1$-$C_6$-alkyl heteroaryl".

"Thioalkoxy" refers to groups —S—R where R includes "$C_1$-$C_6$-alkyl" or "aryl" or "heteroaryl" or "$C_1$-$C_6$-alkyl aryl" or "$C_1$-$C_6$-alkyl heteroaryl". Preferred thioalkoxy groups include thiomethoxy, thioethoxy, and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_1$-$C_6$-alkyl aryl", "$C_1$-$C_6$-alkyl heteroaryl", "$C_2$-$C_6$-alkenyl", "$C_2$-$C_6$-alkynyl", primary, secondary or tertiary amino groups or quarter-nary ammonium moieties, "acyl", "acyloxy", "acylamino", "aminocarbonyl", "alkoxycarbonyl", "aryl", "heteroaryl", carboxyl, cyano, halogen, hydroxy, mercapto, nitro, sulfoxy, sulfonyl, alkoxy, thioalkoxy, trihalomethyl and the like. Alternatively said substitution could also comprise situations where neighboring substituents have undergone ring closure, notably when viccinal functional substituents are involved, thus forming e.g. lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formula I that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and polygalacturonic acid. Said compounds can also be administered as pharmaceutically acceptable quaternary salts known by a person skilled in the art, which specifically include the quarternary ammonium salt of the formula —NR,R',R"+Z−, wherein R, R', R" is independently hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an essentially enantiomeric synthesis or a synthesis comprising an enantioselective step, whereby a surplus of one enantiomer in the order of at least about 52% ee is yielded. In the absence of an enantiomeric synthesis, racemic products are usually obtained that do however also have the inventive set out activity as JunK2 and/or 3 inhibitors.

Quite surprisingly, it was now found that sulfonyl hydrazide derivatives according to formula I are suitable pharmaceutically active agents, by effectively modulating, in particular by down-regulating inhibiting the action of JNK's, notably of JNK 2 and/or 3.

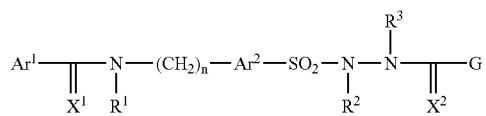

I

In said formula I $Ar^1$ and $Ar^2$ are independently from each other unsubstituted or substituted aryl or heteroaryl;

$X^1$ and $X^2$ are independently from each other O or S;

$R^1$, $R^2$, $R^3$ are independently from each other hydrogen or a $C_1$-$C_6$-alkyl substituent. Alternatively $R^1$ could form a substituted or unsubstituted 5-6-membered saturated or unsaturated ring with $Ar^1$.

According to a further alternative, $R^2$ and $R^3$ could form a substituted or unsubstituted 5-6-membered saturated or unsaturated ring.

n is an integer from 0 to 5, preferably 1 to 3 and most preferred 1.

G is selected from a group comprising or consisting of an unsubstituted or substituted 4-8 membered heterocycle containing at least one heteroatom, or G is a substituted or unsubstituted $C_1$-$C_6$-alkyl group.

The present invention also includes the geometrical isomers, the optical active forms, enantiomers, diastereomers of compounds according to formula I, as well as their racemates and also pharmaceutically acceptable salts as well as the pharmaceutically active derivatives of the sulfonyl hydrazide derivatives of formula I.

According to a particularly preferred embodiment of the present invention, G is

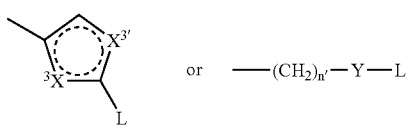

wherein, both $X^3$ and $X^{3'}$ are selected independently from each other from the group consisting of N, O, S or CHL';

Y is O, S or $NR^4$; whereby $R^4$ is H or an unsubstituted or substituted $C_1$-$C_6$-alkyl, an unsubstituted or substituted aryl or heteroaryl;

n' is an integer from 0 to 5, preferably between 1-3 and most preferred 3.

L and L' are independently from each other selected from the group comprising or consisting of H, unsubstituted or substituted $C_1$-$C_6$-aliphatic alkyl, unsubstituted or substituted $C_2$-$C_6$-alkenyl, unsubstituted or substituted $C_2$-$C_6$-alkynyl, unsubstituted or substituted cyclic $C_4$-$C_8$-alkyl, optionally containing 1-3 heteroatoms and optionally fused with aryl or heteroaryl; or L and L' are independently from each other selected from the group comprising or consisting of unsubstituted or substituted aryl or heteroaryl, aryl-$C_1$-$C_6$-alkyl, heteroaryl-$C_1$-$C_6$-alkyl, —C(O)—$OR^5$, —C(O)—$R^5$, —C(O)—$NR^5R^5$, —$NR^5R^5$, —$NR^5C(O)R^5$, —$NR^5C(O)NR^5R^5$, —(SO)$R^5$, —(SO$_2$)$R^5$, —NSO$_2R^5$, —SO$_2NR^5R^5$.

In the above enumeration, $R^5$ and $R^{5'}$ are substituents being independently selected from the group comprising or consisting of H, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted aryl, unsubstituted or substituted heteroaryl, unsubstituted or substituted aryl-$C_1$-$C_6$-alkyl, unsubstituted or substituted heteroaryl-$C_1$-$C_6$-alkyl.

All above mentioned aryl or heteroaryl groups could optionally be substituted by at least one of the following groups: unsubstituted or substituted $C_1$-$C_6$-alkyl, like trihalomethyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, aminoacyl, aminocarbonyl, unsubstituted or substituted $C_1$-$C_6$-alkoxycarbonyl, aryl, carboxyl, cyano, halogen, hydroxy, nitro, sulfoxy, sulfonyl, $C_1$-$C_6$-thioalkoxy.

In preferred sulfonyl hydrazide derivatives according to formula I, $Ar^1$ and/or $Ar^2$ are independently selected from the group consisting of phenyl, thienyl, ftiryl, pyridyl, pyrazolyl, pyrimidinyl, imidazolyl, naphthyl, quinolyl, optionally substituted by unsubstituted or substituted $C_1$-$C_6$-alkyl, in particular tri-halomethyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, acylamino, aminocarbonyl, unsubstituted or substituted $C_1$-$C_6$-alkoxycarbonyl, aryl, carboxyl, cyano, halogen, hydroxy, nitro, sulfoxy, sulfonyl, $C_1$-$C_6$-thioalkoxy. Most preferred sulfonyl hydrazide derivatives according to formula I are those where-in $Ar^1$ is a substituted or unsubstituted phenyl, preferably 4-chlorophenyl and/or $Ar^2$ is a thienyl group.

According to a particularly preferred embodiment, $Ar^1$ is a substituted or unsubstituted phenyl, preferably 4-chlorophenyl, $X^1$ and $X^2$ are O, while $R^1$, $R^2$, $R^3$ are all hydrogen, n is 1, $Ar^2$ is thienyl, G is selected from

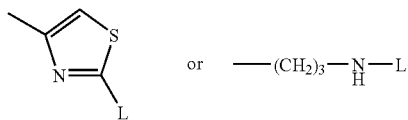

wherein L is selected from the group comprising or consisting of H, substituted or unsubstituted $C_1$-$C_6$-aliphatic alkyl, substituted or unsubstituted cyclic $C_4$-$C_8$-alkyl optionally containing 1-3 heteroatoms and optionally fused with aryl. Also, L could be an unsubstituted or substituted aryl or heteroaryl, aryl-$C_1$-$C_6$-alkyl, heteroaryl-$C_1$-$C_6$-alkyl, —C(O)—$OR^5$, —C(O)—$R^5$, —C(O)—$NR^{5'}R^5$, —$NR^{5'}R^5$, —$NR^{5'}C(O)R^5$, —$NR^{5'}C(O)NR^{5'}R^5$, —(SO)$R^5$, —(SO$_2$)$R^5$.

Thereby, $R^5$ and $R^{5'}$ are substituents being independently selected from the group comprising or consisting of H, unsubstituted or substituted $C_1$-$C_6$-alkyl, unsubstituted or sub-stituted $C_2$-$C_6$-alkenyl, unsubstituted or substituted $C_2$-$C_6$-alkynyl, unsubstituted or substituted aryl, unsubstituted or substituted heteroaryl, unsubstituted or substituted aryl-$C_1$-$C_6$-alkyl, unsubstituted or substituted heteroaryl-$C_1$-$C_6$-alkyl.

Said aryl or heteroaryl groups are optionally substituted by unsubstituted or substituted $C_1$-$C_6$-alkyl, like trihalomethyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, aminoacyl, aminocarbonyl, $C_1$-$C_6$-alkoxycarbonyl, aryl, carboxyl, cyano, halogen, hydroxy, nitro, sulfoxy, sulfonyl, $C_1$-$C_6$-thioalkoxy.

In a particularly preferred embodiment the residue G is

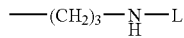

whereby L is as above defined, with most preferred groups L being substituted or unsubstituted pyridyl groups.

Specific examples of compounds of formula I include the following:

4-chloro-N-[(5-{[2-({2-[4-(1,3-dithiolan-2-yl)phenyl]-1,3-thiazol-4-yl}carbonyl)hydrazino]sulfonyl}thien-2-yl)methyl]benzamide 4-chloro-N-{[5-({2-[(2-phenyl-1,3-thiazol-4-yl)carbonyl]hydrazino}sulfonyl)thien-2-yl]methyl}benzamide 4-chloro-N-{[5-({2-[(2-{[(4-chlorophenyl)sulfonyl]methyl}-1,3-thiazol-4-yl)carbonyl]-hydrazino)sulfonyl}thien-2-yl]methyl}benzamide 4-chloro-N-{[5-({2-[(2-methyl-1,3-thiazol-4-yl)carbonyl]hydrazino}sulfonyl)thien-2-yl]methyl}benzamide 4-chloro-N-[(5-{[2-({2-[4-(H-pyrrol-1-yl)phenyl]-1,3-thiazol-4-yl}carbonyl)hydrazino]-sulfonyl}thien-2-yl)methyl]benzamide 4-chloro-N-[(5-{[2-({2-[(4,5-dichloro-1H-imidazol-1-yl)methyl]-1,3-thiazol-4-yl}-carbonyl)hydrazino]sulfonyl}thien-2-yl)methyl]benzamide 4-chloro-N-[(5-{[2-({2-[5-(trifluoromethyl)pyridin-2-yl]-1,3-thiazol-4-yl}carbonyl)-hydrazino]sulfonyl}thien-2-yl)methyl]benzamide 4-chloro-N-[(5-{[2-({2-[3-chloro-5-(trifluoromethyl)pyridin-2-yl]-1,3-thiazol-4-yl}carbonyl)hydrazino]sulfonyl}thien-2-yl)methyl]benzamide 4-chloro-N-[(5-{[2-({2-[2-chloro-4-(trifluoromethyl)phenyl]-1,3-thiazol-4-yl}-carbonyl)hydrazino]sulfonyl}thien-2-yl)methyl]benzamide 4-chloro-N-[(5-{[2-({2-[4-(trifluoromethyl)pyridin-3-yl]-1,3-thiazol-4-yl}-carbonyl)hydrazino]sulfonyl}thien-2-yl)methyl]benzamide 4-chloro-N-({5-[(2-{[2-(2,3-dichlorophenyl)-1,3-thiazol-4-yl]carbonyl}hydrazino)-sulfonyl]thien-2-yl}methyl)benzamide 4-chloro-N-{[5-({2-[(2-{[(2-furylmethyl)sulfonyl]methyl}-1,3-thiazol-4-yl)carbonyl]hydrazino}sulfonyl)thien-2-yl]methyl}benzamide 4-chloro-N-[(5-{[2-({2-[(2-chlorophenoxy)methyl]-1,3-thiazol-4-yl}carbonyl)-hydrazino]sulfonyl}thien-2-yl)methyl]benzamide 4-chloro-N-({5-[(2-{[2-(2,6-dichlorobenzyl)-1,3-thiazol-4-yl]carbonyl}hydrazino)-sulfonyl]thien-2-yl}methyl)benzamide N-[(5-{[2-({2-[4-(1,3-dithiolan-2-yl)phenyl]-1,3-thiazol-4-yl) carbonyl)hydrazino]-sulfonyl}thien-2-yl)methyl]-3-nitrobenzamide N-[(5-{[2-({2-[4-(1,3-dithiolan-2-yl)phenyl]-1,3-thiazol-4-yl}carbonyl)hydrazino]-sulfonyl}thien-2-yl)methyl]-3-methoxybenzamide N-[(5-{[2-({2-[4-(1,3-dithiolan-2-yl)phenyl]-1,3-thiazol-4-yl}carbonyl)hydrazino]-sulfonyl}thien-2-yl)methyl]-4-nitrobenzamide N'-(4-{[3-chloro-5-(trifluoromethyl)pyridin-2-yl]amino}butanoyl)-5-[(1,3-dioxo-1,3-dihydro-2H-isoindol-2-yl)methyl]thiophene-2-sulfonohydrazide N-[(5-{[2-(4-{[3-chloro-5-(trifluoromethyl)pyridin-2-yl]amino}butanoyl)hydrazino]-sulfonyl}thien-2-yl)methyl]-4-nitrobenzamide N-[(5-{[2-(4-{[3-chloro-5-(trifluoromethyl)pyridin-2-yl]amino}butanoyl)hydrazino]sulfonyl}-thien-2-yl)methyl]-3-hydroxybenzamide N-[(5-{[2-(4-{[3-chloro-5-(trifluoromethyl)pyridin-2-yl]amino}butanoyl)hydrazino]sulfonyl}-thien-2-yl)methyl]-2-hydroxybenzamide N-[(5-{[2-(4-{[3-chloro-5-(trifluoromethyl)pyridin-2-yl]amino}butanoyl)hydrazino]-sulfonyl}thien-2-yl)methyl]benzamide N-[(5-{[2-(4-{[3-chloro-5-(trifluoromethyl)pyridin-2-yl]amino}butanoyl)hydrazino]-sulfonyl) thien-2-yl)methyl]-2-furamide N-[(5-{[2-(4-{[3-chloro-5-(trifluoromethyl)pyridin-2-yl]amino}butanoyl)hydrazino]-sulfonyl}thien-2-yl)methyl]-2-thien-2-ylacetamide N-[(5-{[2-(4-{[3-chloro-5-(trifluoromethyl)pyridin-2-yl]amino}butanoyl)hydrazino]-sulfonyl}thien-2-yl)methyl]-1-naphthamide N-[(5-{[2-(4-{[3-chloro-5-(trifluoromethyl)pyridin-2-yl]amino}butanoyl)hydrazino]-sulfonyl}thien-2-yl)methyl]-2-naphthamide N-[(5-{[2-(4-{[3-chloro-5-(trifluoromethyl)pyridin-2-yl]amino}butanoyl)hydrazino]-sulfonyl}thien-2-yl)methyl]-4-methylbenzamide N-[(5-{[2-(4-{[3-chloro-5-(trifluoromethyl)pyridin-2-yl]amino}butanoyl)hydrazino]-sulfonyl}thien-2-yl)methyl]-4-ethylbenzamide 4-tert-butyl-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)hydrazino]-sulfonyl}thien-2-yl)methyl]-2-fluorobenzamide N-[(5-{[2-(4-{[3-chloro-5-(trifluoromethyl)pyridin-2-yl]amino}butanoyl)hydrazino]-sulfonyl}thien-2-yl)methyl]-3-fluorobenzamide N-[(5-{[2-(4-{[3-chloro-5-(trifluoromethyl)pyridin-2-yl]amino}butanoyl)hydrazino]-sulfonyl}thien-2-yl)methyl]-4-fluorobenzamide N-[(5-{[2-(4-{[3-chloro-5-(trifluoromethyl)pyridin-2-yl]amino}butanoyl)hydrazino]-sulfonyl}thien-2-yl)methyl]-2,6-difluorobenzamide N-[(5-{[2-(4-{[3-chloro-5-(trifluoromethyl)pyridin-2-yl]amino}butanoyl)hydrazino]-sulfonyl}thien-2-yl)methyl]-3,5-difluorobenzamide 2-chloro-N-[(5-{[2-(4-{[3-chloro-5-(trifluoromethyl)pyridin-2-yl]amino}butanoyl)hydrazino]sulfonyl}thien-2-yl)methyl]benzamide 3-chloro-N-[(5-{[2-(4-{[3-chloro-5-(trifluoromethyl)pyridin-2-yl]amino}butanoyl)hydrazino]sulfonyl}thien-2-yl)methyl]benzamide N-[(5-{[2-(4-{[3-chloro-5-(trifluoromethyl)pyridin-2-yl]amino}butanoyl)hydrazino]-sulfonyl}thien-2-yl)methyl]-4-iodobenzamide 2,6-dichloro-N-[(5-{[2-(4-{[3-chloro-5-(trifluoromethyl)pyridin-2-yl]amino}butanoyl)-hydrazino]sulfonyl}thien-2-yl)methyl]benzamide 3,5-dichloro-N-[(5-{[2-(4-{[3-chloro-5-(trifluoromethyl)pyridin-2-yl]amino}butanoyl)-hydrazino]sulfonyl}thien-2-yl)methyl]benzamide 2-bromo-N-[(5-{[2-(4-{[3-chloro-5-(trifluoromethyl)pyridin-2-yl]amino}butanoyl)-hydrazino]sulfonyl}thien-2-yl)methyl]benzamide 3-bromo-N-[(5-{[2-(4-{[3-chloro-5-(trifluoromethyl)pyridin-2-yl]amino}butanoyl)-hydrazino]sulfonyl}thien-2-yl)methyl]benzamide 4-bromo-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)hydrazino]-sulfonyl}thien-2-yl)methyl]-2-iodobenzamide N-[(5-{[2-(4-{[3-chloro-5-(trifluoromethyl)pyridin-2-yl]amino}butanoyl)hydrazino]-sulfonyl}thien-2-yl)methyl]-3-nitrobenzamide N-[(5-{[2-(4-{[3-chloro-5-(trifluoromethyl)pyridin-2-yl]amino}butanoyl)hydrazino]-sulfonyl}thien-2-yl)methyl]-2-nitrobenzamide N-[(5-{[2-(4-{[3-chloro-5-(trifluoromethyl)pyridin-2-yl]amino}butanoyl)hydrazino]-sulfonyl}thien-2-yl)methyl]-4-(dimethylamino)benzamide N-[(5-{[2-(4-{[3-chloro-5-(trifluoromethyl)pyridin-2-yl]amino}butanoyl)hydrazino]-sulfonyl}thien-2-yl)methyl]-3-methoxybenzamide N-[(5-{[2-(4-{[3-chloro-5-(trifluoromethyl)pyridin-2-yl]amino}butanoyl)hydrazino]-sulfonyl}thien-2-yl)methyl]-2-methoxybenzamide N-[(5-{[2-(4-{[3-chloro-5-(trifluoromethyl)pyridin-2-yl]amino}butanoyl)hydrazino]sulfonyl}thien-2-yl)methyl]-4-methoxybenzamide N-[(5-{[2-(4-{[3-chloro-5-(trifluoromethyl)pyridin-2-yl]amino}butanoyl)hydrazino]-sulfonyl}thien-2-yl)methyl]-2,6-dimethoxybenzamide N-[(5-{[2-(4-{[3-chloro-5-(trifluoromethyl)pyridin-2-yl]amino}butanoyl)hydrazino]-sulfonyl}thien-2-yl)methyl]-3,5-dimethoxybenzamide N-[(5-{[2-(4-{[3-chloro-5-(trifluoromethyl)pyridin-2-yl]amino}butanoyl)hydrazino]-sulfonyl}thien-2-yl)methyl]-2-(trifluoromethyl)benzamide N-[(5-{[2-(4-{[3-chloro-5-(trifluoromethyl)pyridin-2-yl]amino}butanoyl)hydrazino]-sulfonyl}thien-2-yl)methyl]-3-(trifluoromethyl)benzamide N-[(5-{[2-(4-{[3-chloro-5-(trifluoromethyl)pyridin-2-yl]amino}butanoyl)hydrazino]-sulfonyl}thien-2-yl)methyl]-4-(trifluoromethyl)benzamide N-[(5-{[2-(4-{[3-chloro-5-(trifluoromethyl)pyridin-2-yl]amino}butanoyl)hydrazino]-sulfonyl}thien-2-yl)methyl]-3,5-bis(trifluoromethyl)benzamide N-[(5-{[2-(4-{[3-chloro-5-(trifluoromethyl)pyridin-2-yl]amino}butanoyl)hydrazino]-sulfonyl}thien-2-yl)methyl]nicotinamide N-[(5-{[2-(4-{[3-chloro-5-(trifluoromethyl)pyridin-2-yl]amino}butanoyl)hydrazino]-sulfonyl}thien-2-yl)methyl]isonicotinamide 4-amino-N-[(5-{[2-(4-{[3-chloro-5-(trifluoromethyl)pyridin-2-yl]amino}butanoyl)hydrazino]sulfonyl}thien-2-yl)methyl]benzamide N-[(5-{[2-(4-{[3-chloro-5-(trifluoromethyl)pyridin-2-yl]amino}butanoyl)hydrazino]-sulfonyl}thien-2-yl)methyl]-4-hydroxybenzamide N-[(5-{[2-(4-{[3-chloro-5-(trifluoromethyl)pyridin-2-yl]amino}butanoyl)hydrazino]-sulfonyl}thien-2-yl)methyl]-3,4-dihydroxybenzamide 3,4-diamino-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)hydrazino]-sulfonyl}thien-2-yl)methyl]pyridine-2-carboxamide N-[(5-{[2-(4-{[3-chloro-5-(trifluoromethyl)pyridin-2-yl]amino}butanoyl)hydrazino]-sulfonyl}thien-2-yl)methyl]-6-hydroxypyridine-2-carboxamide 6-amino-N-[(5-{[2-(4-{[3-chloro-5-(trifluoromethyl)pyridin-2-yl]amino}butanoyl)-hydrazino]sulfonyl}thien-2-yl)methyl]nicotinamide N-[(5-{[2-(4-{[3-chloro-5-(trifluoromethyl)pyridin-2-yl]amino}butanoyl)hydrazino]-sulfonyl}thien-2-yl)methyl]-2-sulfanylnicotinamide N-[(5-{[2-(4-{[3-chloro-5-(trifluoromethyl)pyridin-2-yl]amino}butanoyl)hydrazino]-sulfonyl}thien-2-yl)methyl]-6-sulfanylnicotinamide N-[(5-{[2-(4-{[3-chloro-5-(trifluoromethyl)pyridin-2-yl]amino}butanoyl)hydrazino]-sulfonyl}thien-2-yl)methyl]-2,6-dihydroxyisonicotinamide N-[(5-{[2-(4-{[3-chloro-5-(trifluoromethyl)pyridin-2-yl]amino}butanoyl)hydrazino]-sulfonyl}thien-2-yl)methyl]-5-nitro-1H-pyrazole-3-carboxamide N-[(5-{[2-(4-{[3-chloro-5-(trifluoromethyl)pyridin-2-yl]amino}butanoyl)hydrazino]-sulfonyl}thien-2-yl)methyl]-2-hydroxy-6-methoxybenzamide N-[(5-{[2-(4-{[3-chloro-5-(trifluoromethyl)pyridin-2-yl]amino}butanoyl)hydrazino]-sulfonyl}thien-2-yl)methyl]-8-hydroxyquinoline-7-carboxamide 2-amino-N-[(5-{[2-(4-{[3-chloro-5-(trifluoromethyl)pyridin-2-yl]amino}butanoyl)-hydrazino]sulfonyl}thien-2-yl)methyl]nicotinamide N-[(5-{[2-(4-{[3-chloro-5-(trifluoromethyl)pyridin-2-yl]
amino}butanoyl)hydrazino]-sulfonyl}thien-2-yl)methyl]-
4-fluoro-3-nitrobenzamide
2-amino-N-[(5-{[2-(4-{[3-chloro-5-(trifluoromethyl)pyridin-2-yl]amino}butanoyl)-hydrazino]sulfonyl}thien-2-yl)methyl]benzamide
N-[(5-{[2-(4-{[3-chloro-5-(trifluoromethyl)pyridin-2-yl]
amino}butanoyl)hydrazino]-sulfonyl}thien$^{-2}$-yl)methyl]-
2,3,4-trihydroxybenzamide
N-[(5-{[2-(4-{[3-chloro-5-(trifluoromethyl)pyridin-2-yl]
amino}butanoyl)hydrazino]-sulfonyl}thien-2-yl)methyl]-
2-oxo-1,2-dihydropyridine-3-carboxamide
N-[(5-{[2-(4-{[3-chloro-5-(trifluoromethyl)pyridin-2-yl]
amino}butanoyl)hydrazino]-sulfonyl}thien-2-yl)methyl]-
2,4-dihydroxybenzamide
N-[(5-{[2-(4-{[3-chloro-5-(trifluoromethyl)pyridin-2-yl]
amino}butanoyl)hydrazino]-sulfonyl}thien-2-yl)methyl]-
5-hydroxypyridine-2-carboxamide
N-[(5-{[2-(4-{[3-chloro-5-(trifluoromethyl)pyridin-2-yl]
amino}butanoyl)hydrazino]-sulfonyl}thien-2-yl)methyl]-
2,4-dioxo-1,2,3,4-tetrahydropyrimidine-5-carboxamide
N-[(5-{[2-(4-{[3-chloro-5-(trifluoromethyl)pyridin-2-yl]
amino}butanoyl)hydrazino]sulfonyl}thien-2-yl)methyl]-
1H-imidazole-4-carboxamide
4-chloro-N-(4-{[2-(4-{[3-chloro-5-(trifluoromethyl)pyridin-2-yl]amino}butanoyl)hydrazino]sulfonyl}benzyl)
benzamide
4-chloro-N-(2-{[2-(4-{[3-chloro-5-(trifluoromethyl)pyridin-2-yl]amino}butanoyl)-hydrazino]sulfonyl}phenyl)
benzamide
4-chloro-N-(3-{[2-(4-{[3-chloro-5-(trifluoromethyl)pyridin-2-yl]amino}butanoyl)-hydrazino]sulfonyl}phenyl)
benzamide
N-(4-{[2-(4-{[3-chloro-5-(trifluoromethyl)pyridin-2-yl]
amino}butanoyl)hydrazino]-sulfonyl}benzyl)-3-nitrobenzamide
4-chloro-N-(3-{[2-(4-{[3-chloro-5-(trifluoromethyl)pyridin-2-yl]amino}butanoyl)-hydrazino]sulfonyl}benzyl)
benzamide
N-(3-{[2-(4-{[3-chloro-5-(trifluoromethyl)pyridin-2-yl]
amino}butanoyl)hydrazino]-sulfonyl}benzyl)benzamide
N-(3-{[2-(4-{[3-chloro-5-(trifluoromethyl)pyridin-2-yl]
amino}butanoyl)hydrazino]-sulfonyl}benzyl)-2-hydroxybenzamide
N-(3-{[2-(4-{[3-chloro-5-(trifluoromethyl)pyridin-2-yl]
amino}butanoyl)hydrazino]sulfonyl}benzyl)-3-nitrobenzamide Most preferred compounds are selected from thew groups consisting of:
4-chloro-N-[(5-{[2-({2-[4-(1,3-dithiolan-2-yl)phenyl]-1,3-thiazol-4-yl}carbonyl)hydrazino]sulfonyl}thien-2-yl)methyl]benzamide
4-chloro-N-[(5-{[2-({2-[(2-chlorophenoxy)methyl]-1,3-thiazol-4-yl}carbonyl)hydrazino]sulfonyl}thien-2-yl)methyl]benzamide
N-[(5-{[2-(4-{[3-chloro-5-(trifluoromethyl)pyridin-2-yl]
amino}butanoyl)hydrazino]sulfonyl}thien-2-yl)methyl]-
2-hydroxybenzamide
N-[(5-{[2-(4-{[3-chloro-5-(trifluoromethyl)pyridin-2-yl]
amino}butanoyl)hydrazino]sulfonyl}thien-2-yl)methyl]-
2-oxo-1,2-dihydropyridine-3-carboxamide
4-chloro-N-(4-{[2-(4-{[3-chloro-5-(trifluoromethyl)pyridin-2-yl]amino}butanoyl)hydrazino]sulfonyl}benzyl)
benzamide A further aspect of the present invention consists in the use of the sulfonyl hydrazide derivatives according to formula I for the preparation of pharmaceutical compositions for the modulation—notably for the down-regulation, e.g. up to the inhibition—of the JNK function or signalling pathway associated disorders, in particular against neuronal disorders and/or against disorders of the immune system as well as said pharmaceutical compositions themselves. Preferred JNK pathways are the JNK1 and/or JNK2 and/or JNK3.

As pointed out above, the compounds of formula I are suitable to be used as a medicament. Some very few of the compounds falling into the above generic formula I have been disclosed prior to the filing of the present application, but no medical or biological activity whatsoever was unveiled so far. Hence, it is herein reported that both the novel and the few known compounds falling under the above set out generic formula I are indeed suitable for use in treating disorders of the autoimmune system and neuronal system of mammals, notably of human beings. More specifically, the compounds according to formula I, alone or in the form of a pharmaceutical composition, are useful for the modulation of the JNK pathway, more specifically for treatment or prevention of disorders associated with abnormal expression or activity of JNK, notably of JNK1 and/or JNK2 and/or JNK3. Said modulation usually preferably involves the inhibition of the JNK pathways, notably of the JNK1 and/or JNK2 and/or JNK3. Such an abnormal expression or activity of JNK could be triggered by numerous stimuli (e.g. stress, septic schock, oxidative stress, cytokines) and could lead to out-of-control apoptosis or autoimmune diseases that is frequently involved in the below enumerated disorders and disease states. Hence, the compounds according to formula I could be used for the treatment of disorders by modulating the JNK function or signalling pathways. Said modulation of the JNK function or pathways could involve its activation, but preferably it involves the down-regulation up to inhibition of the JNK pathways, notably of the JNK1 and/or JNK2 and/or JNK3. The compounds according to formula I could be employed alone or in combination with further pharmaceutical agents, e.g. with a further JNK modulator.

Specifically, the compounds pursuant to formula I are useful for the treatment or prevention of immuno- and/or neuronal-related diseases or pathological states in which inhibition of JNK2 or JNK3 plays a critical role such as epilepsy; neurodegenerative diseases including Alzheimer's disease, Huntington's disease, Parkinson's disease; retinal diseases; spinal cord injury; head trauma, autoimmune diseases including multiple Sclerosis, inflammatory bowel disease (IBD), rheumatoid arthritis; asthma; septic shock; transplant rejection; cancers including breast, colorectal, pancreatic and cardiovascular diseases including stroke, cerebral ischemia, arterosclerosis, myocordial infarction, myocordial reperfusion injury. Quite surprisingly it turned out that the inventively found compounds according to formula I do show a considerable activity as inhibitors of JNK2 and 3, notably of JNK 3 being involved in neuronal disorders. In a preferred embodiment, the compounds according to the invention are essentially inactive in view of 2 further apoptosis modulating enzymes, i.e. p38 and/or ERK2—belonging incidentally to the same family as JNK2 and 3. Hence, the compounds according to the present invention offer the possibility to come selectively to grips with disorders related to the JNK pathways, while being essentially inefficient with regard to other targets like said p38 and ERK2, so that they could indeed be viewed as selective inhibitors. This is of considerable significance, as these related enzymes are generally involved in different disorders, so that for the treatment of a distinct disorder, it is desired to employ a correspondingly selective medicament.

As a matter of fact, prior to the herein reported, surprisingly found sulfonyl hydrazide derivatives according to formula I, nothing was known in respect of the use of small molecule chemical compounds as inhibitors of the JNK kinase pathway.

Still a further aspect of the present invention consists in the actually novel sulfonyl hydrazide derivatives of formula I, i.e. those JNK inhibiting sulfonyl hydrazide derivatives according to formula I that have not been disclosed by the prior art. As already indicated, a few compounds have been disclosed by the CEREP company (www.cerep.fr) in as far as they are offered in a company catalogue.

The sulfonyl hydrazide derivatives of formula having been disclosed by CEREP, without any biological or pharmaceutical effect though, are those, wherein $Ar^1$ is 4-chlorophenyl, $Ar^2$ is thienyl, $X^1$ and $X^2$ are O, $R^1$, $R^2$ and $R^3$ are H, n is 1 and G is selected from the following group:

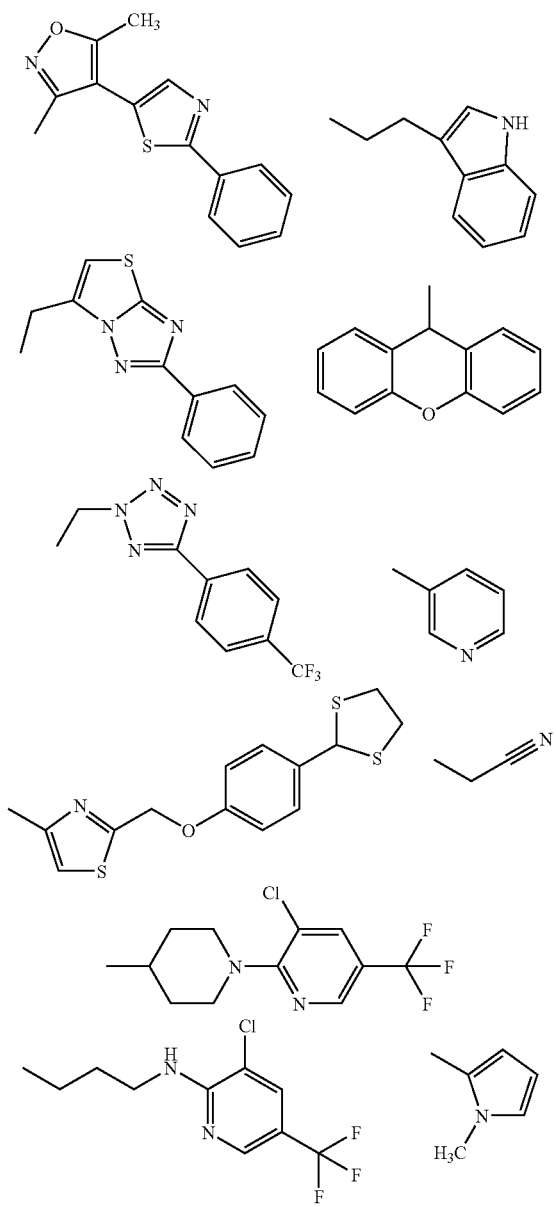

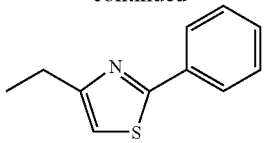

Hence, the entirely novel sulfonyl hydrazide derivatives of formula I are those of the above set out general formula I whereby the above identified known compounds of the CEREP company are excluded.

Still a further object of the present invention is a process for preparing the novel sulfonyl hydrazide derivatives of formula I which have been set out above. The compounds of this invention can be prepared from readily available starting materials using the following general methods and procedures.

It will be appreciated that where typical or preferred experimental conditions (i.e. reaction temperatures, time, moles of reagents, solvents, etc.) are given, other experimental conditions can also be used unless otherwise stated. Optimum reaction conditions may vary with the particular reactants or solvent used, but such conditions can be determined by one skilled in the art by routine optimisation procedures.

According to a preferred method of synthesis, the sulfonyl hydrazide derivatives of the invention are prepared by first coupling an amine of formula II:

$$R^1HN\text{—}(CH_2)_n\text{—}Ar^2 \qquad II$$

where $Ar^2$ and $R^1$ are as defined above, with an acyl chloride of formula III:

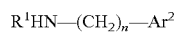

III where $Ar^1$ and $X^1$ are as defined above, to provide an amide of formula IV:

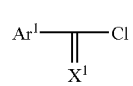

IV

Amines of formula II are either known compounds or can be prepared from known compounds by conventional procedures. Preferred amines as starting materials include thien-2-ylmethylamine, furan-2-ylmethylamine, pyridyl-2-ylmethylamine and the like.

The acyl chlorides of formula III are also commercially available or previously described compounds. Preferred acyl chlorides include 4-chlorobenzoyl chloride, 4-fluorobenzoylchloride, 4-trifluoromethylbenzoyl chloride and the like. If not known, the acid halide can be prepared by reacting the corresponding carboxylic acid with an inorganic acid halide, such as thionyl chloride, phosphorus trichloride or oxalyl chloride under conventional conditions.

Generally, the above set out reaction is conducted using about 1 to 5 molar equivalents of the inorganic acid halide or oxalyl chloride, either neat or in an inert solvent, such as carbon tetrachloride, at a temperature in the range of about 0° C. to about 80° C. for about 1 to about 48 hours. A catalyst, as N,N-dimethylformamide, may also be used in this reaction.

When an acyl halide is employed in the coupling reaction, it is typically reacted with amine II in the presence of a suitable base to scavenge the acid generated during the reaction. Suitable bases include, by way of example, triethylamine, diisopropylethylamine, N-methylmorpholine and the like. Alternatively, an excess of amine II may be used to scavenge the acid generated during the reaction.

Alternatively, the carboxylic acid of compound III can be employed in the coupling reaction. The carboxylic acids of III are usually commercially available reagents or can be prepared by conventional procedures.

The coupling reaction of carboxylic acid of III is conducted using any conventional coupling reagent including, for example, carbodiimides such as dicyclohexylcarbodiimide, N-(3-dimethylaminopropyl)-N'-Ethylcarbodiimide and other promoting agents, such as N,N-carbonyldiimidazole or PyBOP. This reaction can be conducted with or without the use of well known additives such as N-hydroxysuccinimide, 1-hydroxybenzotriazole and the like which are known to facilitate the coupling of carboxylic acids and amines.

The coupling reaction using either acid halide III or its carboxylic acid is preferably conducted at a temperature of from about −70° C. to about 60° C. for about 1 to about 24 hours. Typically, the reaction is conducted in a inert aprotic polar solvent such as dimethylformamide, dichloromethane, chloroform, acetonitrile, tetrahydrofuran and the like using about 1 to about 5 molar equivalents of the amine based on the carboxylic acid or its acid halide. Upon completion of the reaction, the carboxamide IV is recovered by conventional methods including precipitation, chromatography, filtration, distillation and the like. The sulfonyl chlorides of formula V necessary for the preparation of the hydrazides of formula I are either commercially available or prepared using conventional sulfonating methods:

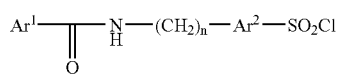

A preferred sulfonating reagent for use in this reaction is chlorosulfonic acid. Typically, the sulfonation reaction is conducted by treating the carboxamide of formula IV with about 5 to about 10 molar equivalent of the sulfonating reagent in an inert solvent, such as dichloromethane, at a temperature ranging from about −70° C. to about 50° C. Preferably, the addition of chlorosulfonic acid takes place at −70° C. and leads to the formation of the interrnediate sulfonic acid. Increasing the temperature to 20° C. allows the formation of the sulfonyl chloride of formula V.

In another preferred method of synthesis and when the above method is not applicable to the preliminary synthesis of sulfonyl chloride of formula V, the sulfonyl hydrazides of this invention are prepared by sequentially:

Protection of the amine function of compounds of formula II

Chlorosulfonylation of the aromatic group

Formation of the sulfonamide function

Deprotection of the protectiong group

Acylation of the above generated free amine

Amines of formula II are protected with a suitable protecting group of an amine moiety to provide intermediate of formula VI wherein P denotes the protecting group.

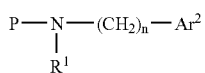

Numerous protecting groups P of the amine function as well as their introduction and removal, are well described in T. W. Greene and G. M. Wuts, Protecting groups in Organic Synthesis, Third Edition, Wiley, New York, 1998, and references cited therein. Preferred are protecting groups that are acids and bases stable and can be further removed by using metal transition complexes such as palladium complexes, for example the allylcarbamate group (Alloc) or the N,N'-bisallyl group. Another preferred protecting group is the maleimide group which is stable in a all range of experimental conditions.

The introduction of said groups can be performed by reacting the corresponding bisallyl-carbonate anhydride or allyl-bromide or maleic anhydride in the presence of a base such as triethylamine, diisopropylethylamine, N-methylmorpholine and the like in an aprotic solvent such as N,N-dimethylformamide, dichloromethane, chloroform, acetonitrile, tetra-hydrofuran and the like at a temperature ranging from about 0° C. to about 80° C.

Compounds of formula VI are then sulfonated using a conventional very mild sulfonating procedure that allows the obtention of sulfonyl chloride of formula VII.

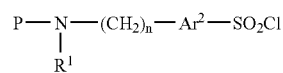

Typically, protected amine VI is treated with a base such as n-butyllithium or tert-butyl-lithium under an inert atmosphere, in a polar aprotic solvent such as tetrahydrofuran, ether or dioxane at a temperature ranging from −70° C. to 0° C. during a time ranging from 15 minutes to 4 hours. The so formed anion is then treated with $SO_2Cl_2$ or most preferably $SO_2$ by bubbling the gas into the reaction mixture at a temperature ranging from −70° C. to 20° C. during a time ranging from 5 minutes to 1 hour. The sulfonate obtained is then transformed "in situ" to the sulfonyl chloride of formula VII by contacting with N-chlorosuccinimide at a temperature ranging from 0° C. to 70° C.

The sulfonyl hydrazide derivatives of formula I are readily prepared from the corresponding sulfonyl chloride V or VII, by reaction with an acyl hydrazide of general formula VIII

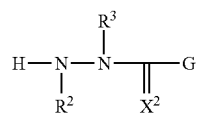

wherein $R^2$, $R^3$, $X^2$ and G are as defined above

For G being selected from the group consisting of an alkylidene group of the formula $-(CH_2)_n-NR^4$-aryl or $-(CH_2)_n-$O-aryl, $-(CH_2)_n-$S-aryl, wherein n is an integer from 1 to 5, and $R^4$ is selected from hydrogen and lower alkyl, a preferred method of synthesis of derivatives of formula VIII, when they are not commercially available, involves in a first step the preparation of compounds of formula IX wherein n', X are as described above

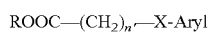

A preferred route is the addition of compounds of type $RO_2C$—$(CH_2)_n$—$NHR^5$—, $RO_2C$—$(CH_2)_n$—OH, $RO_2C$—$(CH_2)_n$—SH—, (R=H, Me) onto an activated chloro-substituted aromatic moiety such as 2-chloro-pyridine, 2-chloropyrimidine and the like. The compounds used are either commercially available or of their preparation is well known by the one skilled in the art compounds. This reaction is performed in the presence of a base such as triethylamine, diisopropylethylamine, N-methylmorpholine, potassium carbonate, cesium carbonate, and the like in a polar protic solvent such as methanol, ethanol and the like at a temperature ranging from about 20° C. to about 180° C.

In case that a reaction of aromatic nucleophilic substitution is not feasible, a further preferred route consists in the addition of suitably substituted phenol or suitably substituted thiophenol onto compounds of type $RO_2C$—$(CH_2)_n$—X, wherein X=Cl, Br, I, OTs, OMs (mesyl) and R=Me.

Another preferred route is the addition of suitably substituted anilines onto compounds of type $RO_2C$—$(CH_2)_n$—X, wherein X=Cl, Br, I, OTs, OMs and R=Me.

In that latter case, anilines may have to be protected in order to increase the nucleophilicity of the nitrogen or to avoid any double alkylation. Preferred is the use of a protecting group which withstands the addition conditions and which can be easily fixed as well as removed, like for instance $CF_3CO$, BOC and the like. Numerous protected group of the amine function of an aniline and their introduction and removal, are well described in T. W. Greene and G. M. Wuts, "*Protecting groups in Organic Synthesis*", Third Edition, Wiley, New York, 1998, and references cited therein.

Compounds of type IX are generally obtained in good yield when the addition is conducted in the presence of a base such as triethylamine, diisopropylethylamine, potassium carbonate and the like in solvent such as N,N-dimethylformamide, dimethylsulfoxide, N-methyl-pyrrolidone, ethanol, acetonitrile at a temperature from about 0° to about 100° C. When one of the above mentioned reactions is leading to the acid derivatives of IX (R=H), an esterification step, of conditions well known of one skilled in the art, is required to afford the ester necessary to obtain compounds of formula VII.

A preferred method of synthesis of derivatives of formula VIII is involving in a second step the addition of low molecular weight hydrazines of type $R^2NH$—$NHR^3$ such as hydrazine, methyl hydrazine, 1,2-dimethylhydrazine and the like onto compounds of type IX (R=Me). This reaction is performed in the presence of a base such as triethylamine, diisopropylethyl-amine, N-methylmorpholine, potassium carbonate, cesium carbonate, and the like in a polar protic solvent such as methanol, ethanol and the like at a temperature ranging from 20° C. to 150° C.

Upon completion of the reaction, the acyl hydrazine VIII is recovered by conventional methods including precipitation, chromatography, filtration, distillation and the like. For G being represented by a group of the formula:

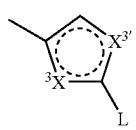

wherein $X^3$, $X^{3'}$ and L are as above defined, a preferred access to derivatives according to formula VII—provided they are not commercially available—involves in a first step the preparation of compounds of formula X.

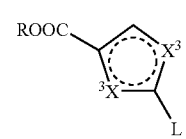

Numerous methods are known in the literature for the preparation of derivatives of formula X depending on the nature of L as extensively described (see: "*Comprehensive Heterocyclic Chemistry II*", 1996, Eds: A. R. Katrisky; C W Ress; E. F. V. Scriven). The acid or ester function of compound X is then transformed into an acylhydrazide group using the methods described for the intermediate of type IX.

The sulfonyl hydrazides of formula I are readily prepared by contacting the sulfonyl chloride V with an amine of formula VIII in the presence of a suitable base to scavenge the acid generated during the reaction. Suitable bases include, by way of examples, triethylamine, diisopropylethylamine, N-methylmorpholine, pyridine and the like. The reaction is preferably conducted in a solvent such as N,N-dimethylformamide, dimethylsulfoxide, N-methylpyrrolidone, ethanol, acetonitrile or chloroform at a temperature from about 0° to about 100° C.

The use of sulfonyl chloride of type VII leads to amines that have to be deprotected using well known methods to afford amine of general formula XI

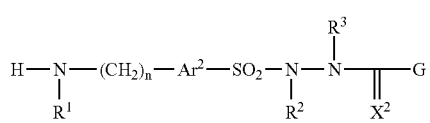

Derivatives of type XI are then acylated according to described methods for the preparation of amides by condensation of amines with acid chlorides or carboxylic acids in the preferred conditions described above leading to compounds of general formula I An alternative method of preparation which has also to be considered as part of this invention, said method of preparation consisting in the condensation of a sulfonyl hydrazide derivative of formula XII

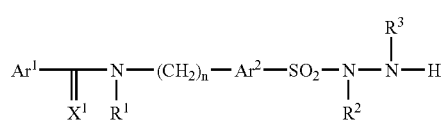

with electrophiles G which will be chosen taking into account parameters known by one skilled in the art. Procedures and methods to perform these types of condensation are well-known and have been well described on various synthesis of sulfonyl hydrazide derivatives. If the above general synthetic methods are not applicable for the obtention of compounds of formula I, suitable methods of preparation known by a person skilled in the art should be used. For example, if $Ar^2$ is phenyl, one should start from commercially available 4-cyanophenyl sulfonyl chloride and applies conventional methods known by a person skilled in the art to reach sulfonyl hydrazide derivatives of formula I.

A final aspect of the present invention is related to the use of the compounds according to formula I for the modulation of the JNK function, or signaling pathways, the use of said compounds for the preparation of pharmaceutical compositions for the modulation of the JNK pathway as well as the formulations containing the active compounds according to formula I. Said modulation of the JNK pathway is viewed as a suitable approach of treatment for various disorders. When employed as pharmaceuticals, the sulfonyl hydrazide derivatives of the present invention are typically administered in the form of a pharmaceutical composition. Hence, pharmaceutical compositions comprising a compound of formula I and a pharmaceutically acceptable carrier, diluent or excipient therefore are also within the scope of the present invention. A person skilled in the art is aware of a whole variety of such carrier, diluent or excipient compounds suitable to formulate a pharmaceutical composition. Also, the present invention provides compounds for use as a medicament. In particular, the invention pro-vides the compounds of formula I for use as JNK inhibitor, notably JNK2 and JNK3, for the treatment of disorders of the immune as well as the neuronal system of mammals, notably of humans, either alone or in combination with other medicaments.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, the sulfonyl hydrazide derivatives of this invention are typically administered in the form of a pharmaceutical composition. Such compositions can be prepared in any manner which is well known in the pharmaceutical art and comprise at least one active compound.

Generally, the compounds of this invention are administered in a pharmaceutically effective amount. The amount of the compound actually administered will be typically determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions containing the sulfonyl hydrazides according to formula I can be administered by a variety of routes including oral, rectal, transdermal, subcutaneous, intravenous, intramuscular, and intranasal. Depending on the intended route of delivery, the compounds are preferably formulated as either injectable or oral compositions.

The compositions containing the sulfonyl hydrazides according to formula I for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the sulfonyl hydrazide derivative of formula I is preferably a minor component (preferably from about 0.1 to about 50% by weight, or more preferably from about 1 to about 40% by weight) with the remainder being various vehicles or carries and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As mentioned before, the sulfonyl hydrazide derivative of formula I in such compositions is typically a minor component, often being from 0.05 to 10% by weight with the remainder being the injectable carrier and the like.

The above described components for orally administered or injectable compositions are merely representative. Further materials as well as processing techniques and the like are set out in Part 8 of *Remington's Pharmaceutical Sciences*, 17$^{th}$ Edition, 1985, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

EXAMPLES

Example 1

4-chloro-N-[(5-{[2-(2{-[4-(1,3-dithiolan-2-yl)phenyl]-1,3-thiazol-4-yl}carbonyl)hydrazino]sulfonyl}thien-2-yl)methyl]benzamide 1

4-Chloro-N-thiophen-2-ylmethyl-benzamide 1a

A solution of 4-chlorobenzoyl chloride (0.114 mol) in 50 ml dry $CH_2Cl_2$ is added over 30 min to a stirred solution of 2-aminomethylthiophene (0.137 mol) and $^iPr_2NEt$ (0.25 mol) in $CH_2Cl_2$ (200 ml) at 0° C. A white solid is formed and the reaction is allowed to warm to room temperature over 1 h. The mixture is diluted with 200 ml of $CH_2Cl_2$, washed twice with HCl aq. (0.1N) and dried over $MgSO_4$. Evaporation of the solvents afforded 28 g (98%) of the title benzamide as a white solid: mp 153-54° C., $^1$H NMR ($CDCl_3$) δ 7.9 (d, J=8.67 Hz, 2H), 7.58 (d, J=8.67 Hz, 2H), 7.44 (dd, J=3.77, 1.13 Hz, 1H), 7.22 (d, J=5.27 Hz, 1H), 7.16 (dd, J=3.39, 5.27 Hz, 1H), 6.62 (br d, 1H), 4.98 (d, J=5.65 Hz, 2H).

5-({[1-(4-Chloro-phenyl)-methanoyl]-amino}-methyl)-thiophene-2-sulfonyl chloride 1b A solution of the thiophene 1b (10 g, 40 mmol) in $CH_2Cl_2$ (500 ml) is treated with a solution of chlorosulfonic acid (20.1 ml, 198 mmol) in $CH_2Cl_2$ (80 ml) at −80° C. The reaction mixture is allowed to reach r.t. over 5 h. The mixture is poured on ice and quickly extracted with $CH_2Cl_2$. The organic layer is dried over $MgSO_4$ and the solvent is evaporated to dryness to yield 8.8 g (63%) of the title sulfonyl chloride as a white powder which is used without further purification: mp 133-35° C., $^1$H NMR (DMSO-d6) δ 9.21 (t, J=6.4 Hz, 1H), 7.87 (d, J=8.67 Hz, 2H), 7.53 (d, J=8.67 Hz, 2H), 6.91 (d, J=3.39 Hz, 1H), 6.77 (d, J=3.39 Hz, 1H), 4.53 (d, J=3.77 Hz, 2H).

4-chloro-N-[(5-{[2-({2-[4-(1,3-dithiolan-2-yl)phenyl]-1,3-thiazol-4-yl}carbonyl)-hydrazino]sulfonyl}thien-2-yl)methyl]benzamide 1

A solution of sulfonyl chloride 1b (1.0 equivalents), 2-[4-(1,3-Dithiolan-2-yl)phenyl]-1,3-thiazole-4-carbohydrazide (1.1 equivalents), and pyridine (1.2-2 equivalents) in $CHCl_3$ is heated to reflux for 2 h. Filtration over $SiO_2$ ($CH_3CN$) and evaporation yielded 80% of the desired sulfonyl hydrazide 1.

Upon using the procedure described in the above example 1 and the appropriate starting material and reagents, the following additional sulfonyl hydrazide derivatives of formula I could be obtained. (If the product crystallises during the reaction, it is collected by filtration).

The following table provides HPLC data and mass spectroscopy data of the mentioned examples.[1,2]

| Example | Name | Rt HPLC | Purity | Gradient HPLC | Mass M + 1 | Mass M |
|---|---|---|---|---|---|---|
| 2 | 4-chloro-N-{[5-({2-[(2-phenyl-1,3-thiazol-4-yl)carbonyl]hydrazino}sulfonyl)thien-2-yl]methyl}-benzamide | 12.93 | 94.8 | b | 533 | 531 |
| 3 | 4-chloro-N-{[5-({2-[(2-{[(4-chlorophenyl)sulfonyl]-methyl}-1,3-thiazol-4-yl)carbonyl]hydrazino}sulfonyl)thien-2-yl]methyl}benzamide | 12.47 | 96.1 | b | not seen | not seen |
| 4 | 4-chloro-N-{[5-({2-[(2-methyl-1,3-thiazol-4-yl)carbonyl]hydrazino}sulfonyl)thien-2-yl]methyl}benzamide | 13.56 | 94.8 | b | 469 | 471 |
| 5 | 4-chloro-N-[(5-{[2-({2-[4-(1H-pyrrol-1-yl)phenyl]-1,3-thiazol-4-yl}carbonyl)hydrazino]sulfonyl}thien-2-yl)methyl]benzamide | 14.23 | 89.6 | b | 598 | not seen |
| 6 | 4-chloro-N-[(5-{[2-({2-[(4,5-dichloro-1H-imidazol-1-yl)methyl]-1,3-thiazol-4-yl}carbonyl)hydrazino]-sulfonyl}thien-2-yl)methyl]benzamide | 11.64 | 96 | b | not seen | not seen |
| 7 | 4-chloro-N-[(5-{[2-({2-[5-(trifluoromethyl)pyridin-2-yl]-1,3-thiazol-4-yl}carbonyl)hydrazino]sulfonyl}-thien-2-yl)methyl]benzamide | 13.73 | 86.9 | b | not seen | not seen |
| 8 | 4-chloro-N-[(5-{[2-({2-[3-chloro-5-(trifluoromethyl)pyridin-2-yl]-1,3-thiazol-4-yl}carbonyl)-hydrazino]sulfonyl}thien-2-yl)methyl]benzamide | 13.27 | 95.1 | b | not seen | not seen |
| 9 | 4-chloro-N-[(5-{[2-({2-[2-chloro-4-(trifluoromethyl)phenyl]-1,3-thiazol-4-yl}carbonyl)-hydrazino]sulfonyl}thien-2-yl)methyl]benzamide | 15.16 | 92.4 | b | 635 | 633 |
| 10 | 4-chloro-N-[(5-{[2-({2-[4-(trifluoromethyl)pyridin-3-yl]-1,3-thiazol-4-yl}carbonyl)hydrazino]-sulfonyl}thien-2-yl)methyl]benzamide | 15.09 | 90.1 | b | not seen | not seen |
| 11 | 4-chloro-N-({5-[(2-{[2-(2,3-dichlorophenyl)-1,3-thiazol-4-yl]carbonyl}hydrazino)sulfonyl]thien-2-yl}methyl)benzamide | 14.46 | 86.6 | b | 601 | 601 |
| 12 | 4-chloro-N-{[5-({2-[(2-{[(2-furylmethyl)sulfanyl]-methyl}-1,3-thiazol-4-yl)carbonyl]hydrazino}-sulfonyl)thien-2-yl]methyl}benzamide | 5.29 | 91.2 | a | 615 | 613 |
| 13 | 4-chloro-N-[(5-{[2-({2-[(2-chlorophenoxy)methyl]-1,3-thiazol-4-yl}carbonyl)hydrazino]sulfonyl}thien-2-yl)methyl]benzamide | 13.62 | 99.5 | b | 597 | 595 |
| 14 | 4-chloro-N-({5-[(2-{[2-(2,6-dichlorobenzyl)-1,3-thiazol-4-yl]carbonyl}hydrazino)sulfonyl]thien-2-yl}methyl)benzamide | 6.48 | 89.8 | a | 615 | not seen |
| 15 | N-[(5-{[2-({2-[4-(1,3-dithiolan-2-yl)phenyl]-1,3-thiazol-4-yl}carbonyl)hydrazino]sulfonyl}thien-2-yl)methyl]-3-nitrobenzamide | 6.03 | 82.8 | a | not seen | not seen |
| 16 | N-[(5-{[2-({2-[4-(1,3-dithiolan-2-yl)phenyl]-1,3-thiazol-4-yl}carbonyl)hydrazino]sulfonyl}thien-2-yl)methyl]-3-methoxybenzamide | 6.00 | 91.7 | a | 633 | 631 |
| 17 | N-[(5-{[2-({2-[4-(1,3-dithiolan-2-yl)phenyl]-1,3-thiazol-4-yl}carbonyl)hydrazino]sulfonyl}thien-2-yl)methyl]-4-nitrobenzamide | 6.01 | 97.2 | a | 648 | 646 |

[1]HPLC conditions: C8 Symmetry a-MeCN, 0.09% TFA, 0 to 100% (10 min)
HPLC conditions: C18 b-MeCN, 0.09% TFA, 0 to 100% (20 min), c-MeCN, 0.09% TFA, 0 to 100% (30 min).
[2]Mass spectrum APCI

Example 18

N'-(4-{[3-chloro-5-(trifluoromethyl)pyridin-2-yl]
amino}butanoyl)-5-[(1,3-dioxo-1,3-dihydro-2H-
isoindol-2-yl)methyl]thiophene-2-sulfonohydrazide
18

N-(Thiophen-2-ylmethyl)-isoindole-1,3-dione 18a

A solution of 2-aminomethyl-thiophene (2.1 ml, 20.5 mmol) in $CHCl_3$ (25 ml) is treated with phthalic anhydride (3.0 g, 20.5 mmol) at r.t. for 5 min, then at reflux for 20 min, whereupon a white powder precipitated out. This powder is collected by filtration and dried in vacuo to give N-thiophen-2-ylmethyl-phthalamic acid (4.42 g, 83%) as white crystals. An aliquot of this phthalamic acid (2.13 g, 8.12 mmol) is dissolved in MeOH (12 ml), treated with $H_2SO_4$ (440 µl, 8.25 mmol) and heated to reflux for 1.5 h, whereupon a white powder precipitated out. This powder is collected by filtration and dried in vacuo to give 1.38 g (70%) of the title phthalimide as white crystals: $^1$H NMR (DMSO-$d_6$) δ7.92-7.82 (m., 4H), 7.42 (dd, J=5.1, 1.2 Hz, 1H), 7.08 (dd, J=4.0, 0.8 Hz, 1H), 6.95 (dd, J=5.1, 3.5 Hz, 1H), 4.92 (s, 2H).

5-(1,3-Dioxo-1,3-dihydro-isoindol-2-ylmethyl)-thiophene-2-sulfonyl chloride 18b A solution of the thiophene 18a (821 mg, 3.37 mmol) in 1,4-dioxane (8.0 ml) is treated with $ClSO_3H$ (1.0 ml, 15.0 mmol) at r.t. for 4 h. the mixture is poured in water (20 ml), and washed with $CH_2Cl_2$ (2×50 ml). The organic layer is discarded. The aqueous layer is diluted with $NaHCO_3$ aq. sat. (100 ml.), treated with TBAF (1.0M in THF, 4.0 ml, 4.0 mmol), and extracted with $CH_2Cl_2$ (3×35 ml). The organic layer is dried ($MgSO_4$) and evaporated to give the corresponding tetrabutylammonium sulfonate intermediate (857 mg, 45%) as a colorless oil. A solution of this tetrabutylammonium sulfonate (174 mg, 0.308 mmol) in $CH_2Cl_2$ (3.4 ml) is treated with triphosgene (46 mg, 0.154 mmol) and DMF (20 µl, 0.259 mmol) for 1.5 h. The reaction mixture is filtered of silica gel, eluting with EtOAc/cyclohexane 1:2, and evaporated to give 81 mg (77%) of the title sulfonyl chloride as white crystals which were used without further purification

4-(3-Chloro-5-trifluoromethyl-pyridin-2-ylamino)-butyric acid hydrazide 18c

A mixture of γ-aminobutyric acid (8.18 g, 79.3 mmol), 2,3-dichloro-5-(trifluoromethyl)-pyridine (11.0 ml, 79.3 mmol), triethylamine (27.6 ml, 198.3 mmol) and methanol (270 ml) is heated at 104° C. in a Parr autoclave (450 ml vessel) with mechanical agitation for 3 h. Evaporation, addition of $CH_2Cl_2$ (200 ml), and filtration allowed to remove the unreacted, insoluble γ-aminobutyric acid (2.5 g). Evaporation, addition of t-BuOMe (200 ml), and filtration allowed to remove most of the $Et_3N.HCl$ salt (4.4 g). The ether solution is filtered through a silica gel plug and concentrated to afford the crude N-substituted γ-aminobutyric acid as its triethylammonium salt. This crude is esterified to the corresponding methyl γ-aminobutyrate by heating to reflux for 1.5 h in methanolic $H_2SO_4$ (1.9M $H_2SO_4$ in MeOH, 50 ml). Concentration to about 30 ml, addition of EtOAc (100 ml) and cyclohexane (100 ml), washing ($NaHCO_3$ sat.; $H_2O$; brine), drying ($Na_2SO_4$) and evaporation afforded 13.8 g (59%) of 4-(3-Chloro-5-trifluoromethyl-pyridin-2-ylamino)-butyric acid, methyl ester as a colorless oil: $^1$H NMR ($CDCl_3$) δ8.18 (d, J=0.9 Hz, 1H), 7.53 (d, J=2.2 Hz, 1H), 5.54-5.42 (br. t, J=6 Hz, 1H), 3.61 (s, 3H), 3.51 (q, J=6.8 Hz, 2H), 2.35 (t, J=7.2 Hz, 2H), 1.92 (quint, J=7.0 Hz, 2H).

A solution of the methyl ester prepared above (5.61 g, 19.0 mmol) in 80% aqueous hydrazine (7 ml) and MeOH (14 ml) is heated to reflux for 2 h. The reaction mixture is diluted with EtOAc (250 ml). The unreacted hydrazine is extracted with a minimum amount of water (3×25 ml) and oxidized with bleach. The organic layer is dried ($Na_2SO_4$), concentrated to 50 ml, and poured into a crystalliser containing 150 ml of cyclohexane. The desired hydrazide rapidly crystallized, and filtration after 2 h afforded 4.24 g (76%) of the title acyl hydrazide as pale yellow needles: $^1$H NMR (DMSO-$d_6$) δ8.96 (br. s, 1H), 8.32 (br s, 1H), 7.94 (d, J=2.1 Hz, 1H), 7.25 (t, J=5.5 Hz, 1H), 4.51 (s, 2H), 3.40 (q, J=6.6 Hz, 2H), 2.07 (t, J=7.6 Hz, 2H), 1.88 (quint, J=7.2, 2H); MS m/z 297 (M+H).

N'-(4-{[3-chloro-5-(trifluoromethylpyridin-2-yl]amino}butanoyl)-5-[(1,3-dioxo-1,3-dihydro-2H-isoindol-2-yl)methyl]thiophene-2-sulfonohydrazide 18

A solution of the sulfonyl chloride 18b (71 mg, 0.208 mmol), the acyl hydrazide 18c (64 mg, 0.216 mmol) and pyridine (30 µl, 0.373 mmol) in $CHCl_3$ (1.0 ml) is stirred overnight at r.t. Filtration over $SiO_2$ ($CH_3CN$) and evaporation gave 110 mg (88%) of the title compound as a colorless powder: $^1$H NMR (DMSO-d6) 10.03 (d, J=3.2 Hz, 1H), 9.94 (d, J=3.2 Hz, 1H), 8.33-8.29 (br. s, 1H), 7.95-7.79 (m, 5H), 7.43 (d, J=3.8 Hz, 1H), 7.23 (br. t, J=5.6 Hz, 1H), 7.12 (d, J=3.8 Hz, 1H), 4.94 (s, 2H), 3.27 (q, J=6.4 Hz, 2H), 2.01 (t, J=7.4 Hz, 2H), 1.61 (quint, J=7.1 Hz, 2H); MS m/z 602 (M+H).

Example 19

N-[(5-{[2-(4-{[3-chloro-5-(trifluoromethyl)pyridin-2-yl]amino}butanoyl)hydrazino]sulfonyl}thien-2-yl)methyl]-4-nitrobenzamide 19 Diallyl-thiophen-2-ylmethylamine 19a A solution of 2-aminomethyl-thiophene (51.4 g, 956 mmol) and i-$Pr_2NEt$ (140 g, 1081 mmol) in $CH_2Cl_2$ (1 l) was placed in a 3-l flask equipped with a condenser and an efficient magnetic agitation. Allyl bromide (115.7 g, 454 mmol) was added, whereupon the moderately exothermic reaction spontaneously reached the reflux temperature after 2 h. The mixture was stirred overnight (16 h), washed ($NaHCO_3$ sat.; brine), dried ($MgSO_4$), and concentrated. The resulting oil was filtered over silica gel (EtOAc:hexane 1:4). The filtrate was concentrated and the filtration was repeated to afford 70.3 g (80%) of the title diallylamine as a brown-yellow oil, clean by NMR: $^1$H NMR ($CDCl_3$) δ7.25 (br. d, J=5.9 Hz, 1H), 6.98 (br. dd, J=5.1, 2.8 Hz, 1H), 6.94-0.92 (m, 1H), 5.99-5.86 (m, 2H), 5.29-5.18 (m, 4H), 3.85 (s, 2H), 3.16 (dd, J=6.3, 0.9 Hz, 4H).

5-Diallylaminomethyl-thiophene-2-sulfonyl chloride 19b

A solution of the allyl-protected thiophene 19a (6.2 g, 32.1 mmol) in $Et_2O$ was cooled to −70° C. by means of an acetone/dry ice bath. A solution of t-BuLi in pentane (21.38 ml, 1.5M, 32.1 mmol) was added over 2 min whereupon the internal temperature momentarily rose to −50° C. and the mixture turned orange. After 10 min., $SO_2$ was bubbled for 2 min, which led to the immediate formation of a thick precipitate. The reaction was allowed to reach 0° C., and a suspension of NCS (4.63 g, 32.1 mmol) in THF (20 ml) was added, whereupon the slurry turned purple. After 45 min at r.t., the mixture was filtered over $SiO_2$, eluting with EtOAc. Evaporation, dilution with EtOAc:hexane 1:5 and filtration over $SiO_2$ gave 5.0 g (53%) of the title sulfonyl chloride 19b as a pale brown oil which was used without further purification.

5-Diallylaminomethyl-thiophene-2-sulfonic acid, N'-[4-(3-chloro-5-trifluoromethyl-pyridin-2-ylamino)-butanoyl]-hydrazide 19c A solution of the sulfonyl chloride 19b (1.2 g, 4.11 mmol), the acyl hydrazide 18c (1.00 g, 3.38 mmol), and pyridine (300 µl, 3.71 mmol) in chloroform (30 ml) was heated to reflux for 2 h. Dilution with EtOAc (100 ml), washing (half-saturated brine; brine), drying ($Na_2SO_4$), and chromatography (EtOAc; cyclohexane 1:2→1:1) gave 1.69 g (89%) of the title sulfonyl hydrazide as a colourless oil: $^1$H NMR ($CDCl_3$) δ9.73 (s, 1H), 8.22 (s, 1H), 7.50 (d, J=2.1 Hz, 1H), 7.37 (d, J=3.6 Hz, 1H), 7.30-7.20 (br. s, 1H), 6.70 (d, J=3.0 Hz, 1H), 7.73-5.57 (m, 2H), 5.46 (t, J=6.0 Hz, 1H), 5.14.95 (m, 4H), 3.59 (s, 2H), 3.36 (q, J=6.7 Hz, 2H), 2.92 (d, J=6.7 Hz, 4H), 2.08 (dd, J=6.3, 6.9 Hz, 2H), 1.73 (quint., J=6.6 Hz, 2H); MS m/z 552 (M+H).

5-(aminomethyl)-N'-(4-{[3-chloro-5-(trifluoromethyl)pyridin-2-yl]amino}butanoyl)thiophene-2-sulfonohydrazide 19d Procedure A. A solution of the bisallylamine 19c (4.0 g, 7.25 mmol), N,N'-dimethylbarbituric acid (NDMBA 2.8 g, 18.1 mmol), and $Pd(PPh_3)_4$ (148.8 mg, 0.13 mmol) in $CH_2Cl_2$ was de-gassed by bubbling argon for 10 min. The reaction was stirred for 3 h at r.t. whereupon the desired amine 19d precipitated as its NDMBA salt. The mixture was diluted with EtOAc (200 ml) and hexane (200 ml) and washed with water (3×50 ml). The combined aqueous phases were freeze-dried, dissolved in a minimal amount of MeOH and chromatographed ($SiO_2$, $CH_2Cl_2$:EtOAc:$NH_4OH$ aq 80:20:5). The chromatography was repeated twice and gave 2.3 g (67%) of the free amine 19d, which was dissolved in refluxing EtOAc (80 ml) and cooled to −18° C. to afford 1.7 g (50%) of 19d as a white powder: $^1$H NMR (DMSO-d6) δ10.02-9.85 (br. s, 1H), 8.248.19 (br. s, 1H), 7.85 (d, J=2.0 Hz, 1H), 7.32 (d, J=3.8 Hz, 1H), 7.20 (t, J=5.7 Hz, 1H), 6.82 (d, J=3.8 Hz, 1H), 5.3-4.3 (br. s, 2H), 3.80 (s, 2H), 3.23 (q, J=6.7 Hz, 2H), 1.96 (t, J=7.5 Hz, 2H), 1.57 (quint, J=7.2 Hz, 2H); MS m/z 472 (M+H).

Procedure B. Alternatively, a solution of the bisallylamine 19c (9.55 g, 17.3 mmol) and NDMBA (5.55 g, 35.5 mmol) in $CH_2Cl_2$ (195 ml) was degassed by bubbling argon for 10 min. Then, $Pd(PPh_3)_4$ (980 mg, 0.85 mmol) was added and the mixture was stirred for 16 h at 23° C. The mixture was concentrated to a gum, dissolved in hot (60° C.) water, and the aqueous phase was washed with a mixture of EtOAc (200 ml) and tBuOMe (200 ml). The organic layer was extracted with more water (2×100 ml). The aqueous phases were individually concentrated on a rotary evaporator, whereupon a gum quickly separated from the mixture. The gum was removed, the aqueous phases were combined, and evaporation was continued to dryness to give 8.8 g (79%) of the NDMBA salt of the title amine, as a white, crisp powder, which could be used without further purification.

N-[(5-{[2-(4-{[3-chloro-5-(trifluoromethyl)pyridin-2-yl]amino}butanoyl)hydrazino]-sulfonyl}thien-2-yl)methyl]-4-nitrobenzamide 19

A 20 mg/ml solution of the 2-aminomethyl-thiophene 19d in pyridine:$CH_2Cl_2$ 1:4 was cooled to −40° C. and treated for 1 h with 0.8 equiv. of 4-nitrophenyl sulfonyl chloride. The reaction mixture was brought to room temperature over 30 min. Evaporation, dilution in $CH_3CN$, filtration over a $SiO_2$ pad, and evaporation afforded the desired amide in typically 50% yield. $^1$H NMR (DMSO-d6) δ10.05 (d, J=3.3 Hz, 1H), 9.90 (d, J=3.3 Hz, 1H), 9.59 (t, J=5.8 Hz, 1H), 8.32 (d, J=8.8 Hz, 2H), 8.32-8.29 (br. s, 1H), 8.08 (d, J=8.8 Hz, 2H), 7.91 (d, J=2.0 Hz, 1H), 7.43 (d, J=3.8 Hz, 1H), 7.22 (t, J=5.6 Hz, 1H), 7.06 (d, J=3.8 Hz, 1H), 4.66 (d, J=5.8 Hz, 2H), 3.28 (q, J=6.4 Hz, 2H), 2.04 (t, J=7.4 Hz, 2H), 1.64 (quint., J=7.1 Hz, 2H).

Example 20

N-[(5-{[2-(4-{[3-chloro-5-(trifluoromethyl)pyridin-2-yl]amino}butanoyl)hydrazino]sulfonyl}thien-2-yl)methyl]-2-hydroxybenzamide 20

Procedure A. A mixture of 3-acetoxybenzoic acid (8.1 mg, 0.0450 mmol), 5-aminomethyl-thiophene 18d (22.3 mg, 0.0473 mmol), 1-hydroxybenzotriazole (HOBt, 4.7 mg, 0.0348 mmol), and N-(3-dimethylaminopropyl)-N'-ethylcarbodiimide (EDC, 8.5 mg, 0.0443 mmol) was dissolved in DMF (0.6 ml) and stirred overnight at r.t. Work-up (AcOEt/$H_2O$; brine/$Na_2SO_4$), concentration, filtration over a silica gel plug (EtOAc) and evaporation gave the intermediate 3-acetoxybenzamide, which was deacetylated by stirring in MeOH (2 ml) and $Et_3N$ (0.4 ml) for 1 h at 55° C. Evaporation gave 28.5 mg (103%) of the title 3-hydroxy-benzamide as a colorless oil.

Procedure B. A solution of the crude NMDBA salt of 18d (3.2 g, "5.1 mmol"), salicylic acid (987 mg, 7.14 mmol), HOBt (966 mg, 7.14 mmol), and EDC (1.37 g, 7.14 mmol) in DMF (69 ml) was stirred for 1 h at 23° C. The mixture was diluted with EtOAc (700 ml) and washed (3×$H_2O$; brine). The aqueous layers were back-extracted with EtOAc (250 ml). The combined organic layers were concentrated and chromatographed (EtOAc:cyclohexane 1:1→2:1) to give 2.18 g (73%) of the title 3-hydroxybenzamide, which was further purified by preparative reverse-phase HPLC($H_2O$:$CH_3CN$ 70:40 →25:75 over 35 min, Rt=31 min) to give 1.50 g (50%) of a white powder: m.p. 174.5-175.5° C. $^1$H NMR (DMSO-d6) δ10.03 (s, 1H), 9.75-9.65 (br. d, 1H), 9.15 (t, J=6.0 Hz, 1H), 8.33-8.29 (br. s, 1H), 7.93 (d, J=2.0 Hz, 1H), 7.42 (d, J=3.8 Hz, 1H), 7.27-21 (m, 4H), 7.01 (d, J=3.8 Hz, 1H), 6.91 (dt, J=7.1, 2.2 Hz), 4.59 (d, J=5.8 Hz, 2H), 2.69 (q, J=7.0 Hz, 2H), 2.04 (t, J=6.9 Hz, 2H), 1.67 (quint, J=7.1 Hz, 2H). $^{13}$C NMR (DMSO-d6) δ169.65, 167.57, 158.49, 154.79, 149.06, 142.54 (q, J=4 Hz, C—C—$CF_3$), 136.39, 132.80, 131.61, 126.91, 124.82, 122.93 (q, J=271 Hz, $CF_3$), 117.66, 116.22, 114.01, 112.91, 112.01 (q, J=33 Hz, C—$CF_3$), 39.19, 36.62, 29.42, 23.35. $^{19}$F NMR (DMSO-d6) δ-59.52 (s). M/Z APCI: 592 (M+1), 590 (M−1). Anal. HPLC: Rt=6.22 min (method a). $C_{24}H_{23}F_3N_4O_7S_3$ Calc.: C: 44.63%. H, 3.8%. N, 11.83%. Found: C, 44.68%, H, 3.59%, N: 11.90%.

Upon using the procedures described in the above examples 18 to 20 and the appropriate starting material and reagents, the following additional sulfonyl hydrazide derivatives of formula I could be obtained.

| Example | Name | Rt HPLC | Purity | Gradient HPLC | Mass M + 1 | Mass M |
|---|---|---|---|---|---|---|
| 21 | N-[(5-{[2-(4-{[3-chloro-5-(trifluoromethyl)pyridin-2-yl]amino}butanoyl)hydrazino]sulfonyl}thien-2-yl)methyl]-3-hydroxybenzamide | 5.34 | 93.4 | a | 592 | 590 |
| 22 | N-[(5-{[2-(4-{[3-chloro-5-(trifluoromethyl)pyridin-2-yl]amino}butanoyl)hydrazino]sulfonyl}thien-2-yl)methyl]benzamide | 17.16 | 91.8 | c | 576 | 574 |
| 23 | N-[(5-{[2-(4-{[3-chloro-5-(trifluoromethyl)pyridin-2-yl]amino}butanoyl)hydrazino]sulfonyl}thien-2-yl)methyl]-2-furamide | 15.84 | 75.8 | c | 566 | 564 |
| 24 | N-[(5-{[2-(4-{[3-chloro-5-(trifluoromethyl)pyridin-2-yl]amino}butanoyl)hydrazino]sulfonyl}thien-2-yl)methyl]-2-thien-2-ylacetamide | 17.04 | 72.1 | c | 596 | 594 |
| 25 | N-[(5-{[2-(4-{[3-chloro-5-(trifluoromethyl)pyridin-2-yl]amino}butanoyl)hydrazino]sulfonyl}thien-2-yl)methyl]-1-naphthamide | 6.4 | 95.7 | a | 626 | 624 |
| 26 | N-[(5-{[2-(4-{[3-chloro-5-(trifluoromethyl)pyridin-2-yl]amino}butanoyl)hydrazino]sulfonyl}thien-2-yl)methyl]-2-naphthamide | 18.68 | 90.8 | c | 626 | 624 |
| 27 | N-[(5-{[2-(4-{[3-chloro-5-(trifluoromethyl)pyridin-2-yl]amino}butanoyl)hydrazino]sulfonyl}thien-2-yl)methyl]-4-methylbenzamide | 17.88 | 80.5 | c | 590 | 588 |
| 28 | N-[(5-{[2-(4-{[3-chloro-5-(trifluoromethyl)pyridin-2-yl]amino}butanoyl)hydrazino]sulfonyl}thien-2-yl)methyl]-4-ethylbenzamide | 18.95 | 83.7 | c | 604 | 602 |
| 29 | 4-tert-butyl-N-[(5-{[2-(4-{[3-chloro-5-(trifluoromethyl)pyridin-2-yl]amino}butanoyl)hydrazino]sulfonyl}thien-2-yl)methyl]benzamide | 20.6 | 85.6 | c | 632 | 630 |
| 30 | N-[(5-{[2-(4-{[3-chloro-5-(trifluoromethyl)pyridin-2-yl]amino}butanoyl)hydrazino]sulfonyl}thien-2-yl)methyl]-2-fluorobenzamide | 17.13 | 82.5 | c | 594 | 592 |
| 31 | N-[(5-{[2-(4-{[3-chloro-5-(trifluoromethyl)pyridin-2-yl]amino}butanoyl)hydrazino]sulfonyl}thien-2-yl)methyl]-3-fluorobenzamide | 17.66 | 93.3 | c | 594 | 592 |
| 32 | N-[(5-{[2-(4-{[3-chloro-5-(trifluoromethyl)pyridin-2-yl]amino}butanoyl)hydrazino]sulfonyl}thien-2-yl)methyl]-4-fluorobenzamide | 17.58 | 86 | c | 594 | 592 |
| 33 | N-[(5-{[2-(4-{[3-chloro-5-(trifluoromethyl)pyridin-2-yl]amino}butanoyl)hydrazino]sulfonyl}thien-2-yl)methyl]-2,6-difluorobenzamide | 17.12 | 85.1 | c | 612 | 610 |
| 34 | N-[(5-{[2-(4-{[3-chloro-5-(trifluoromethyl)pyridin-2-yl]amino}butanoyl)hydrazino]sulfonyl}thien-2-yl)methyl]-3,5-difluorobenzamide | 18.31 | 92.7 | c | 612 | 610 |
| 35 | 2-chloro-N-[(5-{[2-(4-{[3-chloro-5-{trifluoromethyl)pyridin-2-yl]amino}butanoyl)hydrazino]sulfonyl}thien-2-yl)methyl]benzamide | 17.51 | 82.3 | c | 610 | 608 |
| 36 | 3-chloro-N-[(5-{[2-(4-{[3-chloro-5-(trifluoromethyl)pyridin-2-yl]amino}butanoyl)hydrazino]sulfonyl}thien-2-yl)methyl]benzamide | 18.63 | 86.5 | c | 610 | 608 |
| 37 | N-[(5-{[2-(4-{[3-chloro-5-(trifluoromethyl)pyridin-2-yl]amino}butanoyl)hydrazino]sulfonyl}thien-2-yl)methyl]-4-iodobenzamide | 19.07 | 86.8 | c | 702 | 700 |
| 38 | 2,6-dichloro-N-[(5-{[2-(4-{[3-chloro-5-(trifluoromethyl)pyridin-2-yl]amino}butanoyl)hydrazino]sulfonyl}thien-2-yl)methyl]benzamide | 17.92 | 66 | c | 644 | 642 |
| 39 | 3,5-dichloro-N-[(5-{[2-(4-{[3-chloro-5-(trifluoromethyl)pyridin-2-yl]amino}butanoyl)hydrazino]sulfonyl}thien-2-yl)methyl]benzamide | 20.21 | 82.1 | c | 644 | 642 |
| 40 | 2-bromo-N-[(5-{[2-(4-{[3-chloro-5-(trifluoromethyl)pyridin-2-yl]amino}butanoyl)hydrazino]sulfonyl}thien-2-yl)methyl]benzamide | 17.59 | 94.2 | c | 656 | 654 |
| 41 | 3-bromo-N-[(5-{[2-(4-{[3-chloro-5-(trifluoromethyl)pyridin-2-yl]amino}butanoyl)hydrazinol]sulfonyl}thien-2-yl)methyl]benzamide | 18.81 | 93.2 | c | 656 | 654 |
| 42 | 4-bromo-N-[(5-{[2-(4-{[3-chloro-5-(trifluoromethyl)pyridin-2-yl]amino}butanoyl)hydrazino]sulfonyl}thien-2-yl)methyl]benzamide | 18.89 | 83.3 | c | 653 | 651 |
| 43 | N-[(5-{[2-(4-{[3-chloro-5-(trifluoromethyl)pyridin-2-yl]amino}butanoyl)hydrazino]sulfonyl}thien-2-yl)methyl]-2-iodobenzamide | 17.92 | 92.8 | c | 702 | 700 |
| 44 | N-[(5-{[2-(4-{[3-chloro-5-(trifluoromethyl)pyridin-2-yl]amino}butanoyl)hydrazino]sulfonyl}thien-2-yl)methyl]-3-nitrobenzamide | 16.81 | 69.8 | c | 621 | 619 |
| 45 | N-[(5-{[2-(4-{[3-chloro-5-(trifluoromethyl)pyridin-2-yl]amino}butanoyl)hydrazino]sulfonyl}thien-2-yl)methyl]-2-nitrobenzamide | 17.58 | 93.3 | c | 621 | 619 |

-continued

| Example | Name | Rt HPLC | Purity | Gradient HPLC | Mass M + 1 | Mass M |
|---|---|---|---|---|---|---|
| 46 | N-[(5-{[2-(4-{[3-chloro-5-(trifluoromethyl)pyridin-2-yl]amino}butanoyl)hydrazino]sulfonyl}thien-2-yl)methyl]-4-(dimethylamino)benzamide | 11.97 | 82.3 | b | 610 | 608 |
| 47 | N-[(5-{[2-(4-{[3-chloro-5-(trifluoromethyl)pyridin-2-yl]amino}butanoyl)hydrazino]sulfonyl}thien-2-yl)methyl]-3-methoxybenzamide | 17.61 | 82.9 | c | 606 | 604 |
| 48 | N-[(5-{[2-(4-{[3-chloro-5-(trifluoromethyl)pyridin-2-yl]amino}butanoyl)hydrazino]sulfonyl}thien-2-yl)methyl]-2-methoxybenzamide | 17.31 | 87.4 | c | 606 | 604 |
| 49 | N-[(5-{[2-(4-{[3-chloro-5-(trifluoromethyl)pyridin-2-yl]amino}butanoyl)hydrazino]sulfonyl}thien-2-yl)methyl]-4-methoxybenzamide | 17.03 | 85.4 | c | 606 | 604 |
| 50 | N-[(5-{[2-(4-{[3-chloro-5-(trifluoromethyl)pyridin-2-yl]amino}butanoyl)hydrazino]sulfonyl}thien-2-yl)methyl]-2,6-dimethoxybenzamide | 16.51 | 94.5 | c | 636 | 634 |
| 51 | N-[(5-{[2-(4-{[3-chloro-5-(trifluoromethyl)pyridin-2-yl]amino}butanoyl)hydrazino]sulfonyl}thien-2-yl)methyl]-3,5-dimethoxybenzamide | 17.68 | 89.3 | c | 636 | 634 |
| 52 | N-[(5-{[2-(4-{[3-chloro-5-(trifluoromethyl)pyridin-2-yl]amino}butanoyl)hydrazino]sulfonyl}thien-2-yl)methyl]-2-(trifluoromethyl)benzamide | 18.11 | 72.7 | c | 644 | 642 |
| 53 | N-[(5-{[2-(4-{[3-chloro-5-(trifluoromethyl)pyridin-2-yl]amino}butanoyl)hydrazino]sulfonyl}thien-2-yl)methyl]-3-(trifluoromethyl)benzamide | 19.21 | 91 | c | 644 | 642 |
| 54 | N-[(5-{[2-(4-{[3-chloro-5-(trifluoromethyl)pyridin-2-yl]amino}butanoyl)hydrazino]sulfonyl}thien-2-yl)methyl]-4-(trifluoromethyl)benzamide | 19.32 | 92.2 | c | 644 | 642 |
| 55 | N-[(5-{[2-(4-{[3-chloro-5-(trifluoromethyl)pyridin-2-yl]amino}butanoyl)hydrazino]sulfonyl}thien-2-yl)methyl]-3,5-bis(trifluoromethyl)benzamide | 21.36 | 85.3 | c | 712 | 710 |
| 56 | N-[(5-{[2-(4-{[3-chloro-5-(trifluoromethyl)pyridin-2-yl]amino}butanoyl)hydrazino]sulfonyl}thien-2-yl)methyl]nicotinamide | 3.98 | 90.2 | a | 577 | 575 |
| 57 | N-[(5-{[2-(4-{[3-chloro-5-(trifluoromethyl)pyridin-2-yl]amino}butanoyl)hydrazino]sulfonyl}thien-2-yl)methyl]isonicotinamide | 4.33 | 93.1 | a | 577 | 575 |
| 58 | 4-amino-N-[(5-{[2-(4-{(3-chloro-5-(trifluoromethyl)pyridin-2-yl]amino}butanoyl)hydrazino]-sulfonyl}thien-2-yl)methyl]benzamide | 4.77 | 89.9 | a | 591 | 589 |
| 59 | N-[(5-{[2-(4-{[3-chloro-5-(trifluoromethyl)pyridin-2-yl]amino}butanoyl)hydrazino]sulfonyl}thien-2-yl)methyl]-4-hydroxybenzamide | 5.2 | 88.8 | a | 592 | 590 |
| 60 | N-[(5-{[2-(4-{[3-chloro-5-(trifluoromethyl)pyridin-2-yl]amino}butanoyl)hydrazino]sulfonyl}thien-2-yl)methyl]-3,4-dihydroxybenzamide | 4.98 | 99.1 | a | 608 | 606 |
| 61 | 3,4-diamino-N-[(5-{[2-(4-{[3-chloro-5-(trifluoro-methyl)pyridin-2-yl]amino}butanoyl)hydrazino]-sulfonyl}thien-2-yl)methyl]benzamide | 4.27 | 83.8 | a | 606 | 604 |
| 62 | N-[(5-{[2-(4-{[3-chloro-5-(trifluoromethyl)pyridin-2-yl]amino}butanoyl)hydrazinolsulfonyl}thien-2-yl)methyl]pyridine-2-carboxamide | 5.64 | 99.6 | a | 577 | 575 |
| 63 | N-[(5-{[2-(4-{[3-chloro-5-(trifluoromethyl)pyridin-2-yl]amino}butanoyl)hydrazino]sulfony1}thien-2-yl)methyl)-6-hydroxypyridine-2-carboxamide | 4.85 | 99.3 | a | 593 | 591 |
| 64 | 6-amino-N-[(5-{[2-(4-{[3-chloro-5-(trifluoro-methyl)pyridin-2-yl]amino}butanoyl)hydrazino]-sulfonyl}thien-2-yl)methyl]nicotinamide | 4.22 | 94.5 | a | 592 | 590 |
| 65 | N-[(5-{[2-(4-{[3-chloro-5-(trifluoromethyl)pyridin-2-yl]amino}butanoyl)hydrazino]sulfonyl}thien-2-yl)methyl]-2-sulfanylnicotinamide | 5.21 | 97.2 | a | 609 | 607 |
| 66 | N-[(5-{[2-(4-{[3-chloro-5-(trifluoromethyl)pyridin-2-yl]amino}butanoyl)hydrazino]sulfonyl}thien-2-yl)methyl]-6-sulfanylnicotinamide | 5.01 | 97.8 | a | 609 | 607 |
| 67 | N-[(5-{[2-(4-{[3-chloro-5-(trifluoromethyl)pyridin-2-yl]amino}butanoyl)hydrazino]sulfonyl}thien-2-yl)methyl]-2,6-dihydroxyisonicotinamide | 4.53 | 97.9 | a | 609 | 607 |
| 68 | N-[(5-{[2-(4-{[3-chloro-5-(trifluoromethyl)pyridin-2-yl]amino}butanoyl)hydrazino]sulfonyl}thien-2-yl)methyl]-5-nitro-1H-pyrazole-3-carboxamide | 5.52 | 93.4 | a | 611 | 609 |
| 69 | N-[(5-{[2-(4-{[3-chloro-5-(trifluoromethyl)pyridin-2-yl]amino}butanoyl)hydrazino]sulfonyl}thien-2-yl)methyl]-2-hydroxy-6-methoxybenzamide | 6.04 | 99.3 | a | 622 | 620 |
| 70 | N-[(5-{[2-(4-{[3-chloro-5-(trifluoromethyl)pyridin-2-yl]amino}butanoyl)hydrazino]sulfonyl}thien-2-yl)methyl]-8-hydroxyquinoline-7-carboxamide | 4.32 | 95.4 | a | 643 | 641 |

-continued

| Example | Name | Rt HPLC | Purity | Gradient HPLC | Mass M + 1 | Mass M |
|---|---|---|---|---|---|---|
| 71 | 2-amino-N-[(5-{[2-(4-{[3-chloro-5-(trifluoro-methyl)pyridin-2-yl]amino}butanoyl)hydrazino]-sulfonyl}thien-2-yl)methyl]nicotinamide | 4.28 | 99.3 | a | 592 | 590 |
| 72 | N-[(5-{[2-(4-{[3-chloro-5-(trifluoromethyl)pyridin-2-yl]amino}butanoyl)hydrazino]sulfonyl}thien-2-yl)methyl]-4-fluoro-3-nitrobenzamide | 6.11 | 88.2 | a | 639 | 637 |
| 73 | 2-amino-N-[(5-{[2-(4-{[3-chloro-5-(trifluoro-methyl)pyridin-2-yl]amino}butanoyl)hydrazino]-sulfonyl}thien-2-yl)methyl]benzamide | 5.30 | 90.6 | a | 591 | 589 |
| 74 | N-[(5-{[2-(4-{[3-chloro-5-(trifluoromethyl)pyridin-2-yl]amino}butanoyl)hydrazino]sulfonyl}thien-2-yl)methyl]-2,3,4-trihydroxybenzamide | 5.21 | 58.0 | a | 624 | 622 |
| 75 | N-[(5-{[2-(4-{[3-chloro-5-(trifluoromethyl)pyridin-2-yl]amino}butanoyl)hydrazino]sulfonyl}thien-2-yl)methyl]-2-oxo-1,2-dihydropyridine-3-carboxamide | 4.46 | 77.7 | a | 593 | 591 |
| 76 | N-[(5-{[2-(4-{[3-chloro-5-(trifluoromethyl)pyridin-2-yl]amino}butanoyl)hydrazino]sulfonyl}thien-2-yl)methyl]-2,4-dihydroxybenzamide | 5.56 | 96.6 | a | 608 | 606 |
| 77 | N-[(5-{[2-(4-{[3-chloro-5-(trifluoromethyl)pyridin-2-yl]amino}butanoyl)hydrazino]sulfonyl}thien-2-yl)methyl]-5-hydroxypyridine-2-carboxamide | 6.09 | 99.3 | a | 593 | 591 |
| 78 | N-[(5-{[2-(4-{[3-chloro-5-(trifluoromethyl)pyridin-2-yl]amino}butanoyl)hydrazino]sulfonyl}thien-2-yl)methyl]-2,4-dioxo-1,2,3,4-tetrahydropyrimidine-5-carboxamide | 4.70 | 88.0 | a | 610 | 608 |
| 79 | N-[(5-{[2-(4-{[3-chloro-5-(trifluoromethyl)pyridin-2-yl]amino}butanoyl)hydrazino]sulfonyl}thien-2-yl)methyl]-1H-imidazole-4-carboxamide | 4.21 | 94.6 | a | 566 | 564 |

Example 80

Preparation of 4-chloro-N-(4-{[2-(4-{[3-chloro-5-(trifluoromethyl)pyridin-2-yl]amino}butanoyl)hydrazino]sulfonyl}benzyl)benzamide 80

4-(aminomethyl)-N'-(4-{[3-chloro-5-(trifluoromethyl)pyridin-2-yl]amino}butanoyl)benzenesulfonohydrazide 80a A solution of 4-cyanobenzenesulfonyl chloride (315.5 mg, 1.56 mmol), the acyl hydrazide 18c (509.2 mg, 1.72 mmol), and pyridine (242 ml, 3.12 mmol) in $CHCl_3$ (20 ml) is heated to reflux for 40 min, cooled by means of an ice-bath, and the precipitate is collected by filtration and dried in vacuo to afford 302.7 mg (53%) of the intermediate nitrile as a white powder. A solution of this nitrile (275.7 mg, 0.596 mmol) in THF (10 ml) is treated with a solution of $LiAH_4$ in THF (1.0M, 1.19 ml, 1.19 mmol) for 10 min at r.t., whereupon a thick material precipitates. The reaction mixture is cooled to 0° C., quenched with MeOH (2.0 ml), and treated with conc. aq. HCl (1.0 ml) for 2 h, whereupon the precipitate is dissolved. Concentration and HPLC (reverse-phase C18, gradient $H_2O$: $CH_3CN$:TFA 100:0:0.1→0:100:0.1) and lyophilization gives 94.6 mg (27%) of the TFA salt of the title compound as white powder: $^1H$ NMR ($CD_3OD$) 8.21-8.15 (br. s, 1H), 7.90 (d, J=8.3 Hz, 2H), 7.78 (d, J=1.8 Hz, 1H), 7.62 (d, J=8.3 Hz, 2H), 4.19-4.13 (br. s, 2H), 3.40 (q, J=6.7 Hz, 2H), 2.12 (t, J=7.4 Hz, 2H), 1.73 (quint, J=7.1 Hz, 2H).

4-chloro-N-(4-{[2-(4-{[3-chloro-5-(trifluoromethyl)pyridin-2-yl]amino}butanoyl)hydrazino]sulfonyl}benzyl)benzamide 80

The trifluorocetic acid salt of the aminomethylbenzene 80a (37.8 mg, 0.0652 mmol) is dissolved in pyridine (0.8 ml) and treated with 4-chlorobenzoyl chloride (6.70 μl, 0.0542 mmol) for 2 h. Analytical HPLC indicates the presence of the desired title benzamide as well as of the undesired trifluoroacetamide (arising presumably from the in situ formation of the mixed trifluoroacetic 4-chlorobenoic anhydride) in 1:2 ratio. HPLC (reverse-phase C18, gradient $H_2O$:$CH_3CN$:TFA 100:0:0.1→0:100:0.1) separation and lyophilisization gives 9.0 mg (23%) of the TFA salt of the title compound as an off-white solid: $^1H$ NMR (DMSO-$d_6$) 10.96 (d, J=3.1 Hz, 1H), 9.74 (d, J=3.1 Hz, 1H), 9.21 (t, J=5.7 Hz, 1H), 8.32-8.29 (br. s, 1H), 7.94 (d, J=2.0 Hz, 1H), 7.91 (d, J=8.6 Hz, 2H), 7.75 (d, J=8.3 Hz, 2H), 7.54 (d, J=8.6 Hz, 2H), 7.45 (d, J=8.3 Hz, 2H), 7.23 (t, J=5.6 Hz, 1H), 4.52 (d, J=5.9 Hz, 2H), 3.29 (q, J=6.4 Hz, 2H), 1.95 (t, J=7.4 Hz, 2H), 1.63 (quint, J=7.1 Hz, 2H); MS m/z 472 (M+H).

Example 81

Preparation of 4-chloro-N-(2-{[2-(4-{[3-chloro-5-(trifluoromethyl)pyridin-2-yl]amino}butanoyl)hydrazino]sulfonyl}phenyl)benzamidezide 81

2-Nitro-benzenesulfonyl-N'-[4-(3-chloro-5-trifluoromethyl-pyridin-2-ylamino)-butanoyl]-hydrazide 81a A solution of 2-nitrobenzenesulfonyl chloride (55.3 mg, 0.249 mmol), the acyl hydrazide 18c (70.5 mg, 0.249 mmol), and 4-(dimethylamino)pyridine (DMAP, 122.16 mg, 0.417 mmol) in DMF (1.5 ml) is stirred for 2 h at r.t.. Upon dilution with EtOAc (20 ml) DMAP.HCl precipitates out. Washing (0.1N $HCl_{aq}$; brine), drying ($MgSO_4$), and evaporation gives 96.1 mg (80%) of the title nitrobenzenesulfonamide as a yellow wax that is used without further purification: $^1H$ NMR (DMSO-$d_6$) 10.19 (d, J=2.7 Hz, 1H), 10.10 (d, J=2.7 Hz, 1H), 8.31-8.30 (s, 1H), 8.05 (dd, J=7.2, 1.8 Hz, 1H), 7.95-7.92 (m, 2H), 7.84 (ddd, J=9.3, 7.5, 1.8 Hz, 1H), 7.81 (ddd, J=9.0, 7.2, 1.5 Hz, 1H), 7.27 (br. t, J=5.6 Hz, 1H), 3.32 (q, J=6.5 Hz, 2H), 2.06 (t, J=7.5 Hz, 2H), 1.65 (quint, J=7.2 Hz, 2H).

2-Amino-benzenesulfonyl-N'-[4-(3-chloro-5-trifluoromethyl-pyridin-2-ylamino)-butanoyl]-hydrazide 81b A solution of the nitrobenzenesulfonamide 81a (101.2 mg, 0.210 mmol) and $SnCl_2 \cdot 2H_2O$ (58.8 mg, 0.261 mmol) in DMF (2.0 ml) is stirred overnight at r.t.. As the reaction is incomplete, more $SnCl_2 \cdot 2H_2O$ (58.0 mg, 0.261) is added. After 2 h, the mixture is diluted with EtOAc, filtered over a $SiO_2$ plug, and chromatographed ($SiO_2$, $CH_2Cl_2$:EtOAc 3:1→1:1) to give 62.7 mg (75%) of the title aniline as a pale yellow powder: $^1H$ NMR (DMSO-$d_6$) 10.07 (d, J=3.0 Hz, 1H), 9.74 (d, J=2.7 Hz, 1H), 8.87 (d, J=1.2 Hz, 1H), 8.64-8.61 (br. s, 1H), 8.33-7.99 (br. s, 1H), 7.93 (d, J=2.1 Hz, 1H), 7.56 (dd, J=1.1, 8.0 Hz, 1H), 7.44 (br. t, J=7.7 Hz, 1H), 7.26 (d, J≈8.1 Hz, 1H), 7.23 (t, J≈6.0 Hz, 1H), 6.77 (t, J=7.4 Hz, 1H), 3.26 (buried q, 2H), 2.02 (t, J=7.5, Hz, 2H), 1.62 (quint, J=7.1 Hz, 2H).

4-chloro-N-(2-{[2-(4-{[3-chloro-5-(trifluoromethyl)pyridin-2-yl]amino}butanoyl)hydrazino]sulfonyl}phenyl)benzamide 81

A suspension of the aniline 81b (88.3 μg, 0.195 mmol) in $CH_2Cl_2$ (5.0 mmol) is dissolved with DMF (0.3 ml) and treated with $Et_3N$ (54 μl, 0.387 mmol) and 4-chlorobenzoyl chloride (25 ml, 0.191 mmol) at r.t. for 10 min. Filtration over a $SiO_2$ plug, concentration, and chromatography (EtOAc/hexane 1:3→1:1) affords 34.9 mg (30%) of the title benzamide as a pale yellow oil that can be crystallised from EtOAc/hexane at −18° C.: $^1H$ NMR (DMSO-$d_6$) 10.65 (s, 1H), 10.20 (d, J=2.7 Hz, 1H), 10.10 (d, J=2.7 Hz, 1H), 8.34 (s, 1H), 8.16 (d, J=8.4 Hz, 2H), 7.98 (d, J=2.1 Hz, 1H), 7.80 (dd, J=1.2, 7.8 Hz), 7.73 (d, J=8.7 Hz, 2H), 7.64 (t, J=9.0, 1H), 7.38 (d, J=8.1 Hz, 1H), 7.33-7.26 (br. t, J=5.4 Hz, 1H), 7.16 (t, J=7.5 Hz, 1H), 3.35 (q, J=6.6 Hz, 2H), 2.09 (t, J=7.5, Hz, 2H), 1.62 (quint, J=7.1 Hz, 2H).); MS m/z 590 (M+H).

Upon using the procedures described in the above examples 18 and 18 and the appropriate starting material and reagents, the following additional sulfonyl hydrazide derivatives of formula I could be obtained.

Example 88

Preparation of a Pharmaceutical Formulation

The following formulation examples illustrate representative pharmaceutical compositions of this invention. The present invention, however, is not limited to the following pharmaceutical compositions.

Formulation 1—Tablets

A compound of formula I is admixed as a dry powder with a dry gelatin binder in an approximate 1:2 weight ration. A minor amount of magnesium stearate is added as a lubricant. The mixture is formed into 240-270 mg tablets (80-90 mg of active sulfonyl hydrazide derivative according to formula I per tablet) in a tablet press.

Formulation 2—Capsules

A compound of formula I is admixed as a dry powder with a starch diluent in an approximate 1:1 weight ratio. The mixture is filled into 250 mg capsules (125 mg of active sulfonyl hydrazide derivative according to formula I per capsule).

Formulation 3—Liquid

A compound of formula I (1250 mg), sucrose (1.75 g) and xanthan gum (4 mg) are blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

The compound of formula I is admixed as a dry powder with a dry gelatin binder in an approximate 1:2 weight ratio. A minor amount of magnesium stearate is added as a lubricant. The mixture is formed into 450-900 mg tablets (150-300 mg of active sulfonyl hydrazide derivative according to formula I) in a tablet press.

Formulation 5—Injection

The compound of formula I is dissolved in a buffered sterile saline injectable aqueous medium to a concentration of approximately 5 mg/ml.

In the following the present invention shall be illustrated by means of some examples which are not construed to be viewed as limiting the scope of the invention.

| Example | Name | Rt HPLC | Purity | Gradient HPLC | Mass M + 1 | Mass M |
|---|---|---|---|---|---|---|
| 82 | 4-chloro-N-(3-{[2-(4-{[3-chloro-5-(trifluoromethyl-)pyridin-2-yl]amino}butanoyl)hydrazino]sulfonyl}-phenyl)benzamide | | — | | 590 | 588 |
| 83 | N-(4-{[2-(4-{[3-chloro-5-(trifluoromethyl)pyridin-2-yl]amino}butanoyl)hydrazino]sulfonyl}benzyl)-3-nitrobenzamide | 5.98 | 94.5 | a | 615 | 613 |
| 84 | 4-chloro-N-(3-{[2-(4-{[3-chloro-5-(trifluoromethyl)-pyridin-2-yl]amino}butanoyl)hydrazino]sulfonyl}benzyl)benzamide | 6.46 | 84.5 | a | 604 | 602 |
| 85 | N-(3-{[2-(4-{[3-chloro-5-(trifluoromethyl)pyridin-2-yl]amino}butanoyl)hydrazino]sulfonyl}benzyl)benzamide | 5.74 | 90.5 | a | 570 | 568 |
| 86 | N-(3-{[2-(4-{[3-chloro-5-(trifluoromethyl)pyridin-2-yl]amino}butanoyl)hydrazino]sulfonyl}benzyl)-2-hydroxybenzamide | 6.08 | 76.7 | a | 586 | 584 |
| 87 | N-(3-{[2-(4-{[3-chloro-5-(trifluoromethyl)pyridin-2-yl]amino}butanoyl)hydrazino]sulfonyl}benzyl)-3-nitrobenzamide | 5.9 | 82.3 | a | 615 | 613 |

Example 89

Biological Assays

Biological Results

The activities of the sulfonamide derivatives claimed in the formula I were assessed using the above described in vitro and in vivo biological assays.

JNK 2 and 3 in vitro assays: JNK3 and/or 2 assays are performed in 96 well MTT plates, by incubation of 0.5 µg of recombinant, pre-activated GST-JNK3 or GST-JNK2 with 1 µg of recombinant, biotinylated GST-c-Jun and 2 µM $^{33}\gamma$-ATP (2 nCi/µl), in the presence or absence of sulfonamide inhibitors if formula I and in a reaction volume of 50 µl containing 50 mM Tris-HCl, pH 8.0; 10 mM $MgCl_2$; 1 mM Dithiothreitol, and 100 µM $NaVO_4$. The incubation is performed for 120 min. at R.T and stopped upon addition of 200 µl of a solution containing 250 µg of Streptavidine-coated SPA beads (Amersham, Inc.)*, 5 mM EDTA, 0.1% Triton X-100 and 50 µM ATP, in phosphate saline buffer. After incubation for 60 minutes at RT, beads are sedimented by centrifugation at 1500×g for 5 minutes, resuspended in 200 µl of PBS containing 5 mM EDTA, 0.1% Triton X-100 and 50 µM ATP and the radioactivity measured in a scintillation β counter, following sedimentation of the beads as described above. By substituting GST-c Jun for biotinylated $GST_{-1}ATF_2$ or myelin basic protein, this assay can be used to measure inhibition of preactivated p38 and ERK MAP Kinases, respectively.

| Example | JNK3 | JNK2 | p38 | ERK2 |
| --- | --- | --- | --- | --- |
| 1 | 0.21 | 0.37 | >30 | >30 |
| 13 | 0.31 | 0.97 | >30 | >30 |
| 20 | 0.25 | 0.45 | >30 | >30 |
| 75 | 0.41 | 0.56 | >30 | >30 |
| 80 | 0.25 | 1.02 | >30 | >30 |

The values indicated in respect of JNK2 and 3, p38 and ERK2 refer to the $IC_{50}$ (µM), i.e. the amount necessary to achieve 50% inhibition of said target (e.g. JNK2). From the above table it could be derived that said test compounds according to formula I do have a significant effect both on JNK2 and 3, but virtually no effect onto p38 and ERK2, thus delivering a quite selective inhibitory effect.

Sympathetic Neuron Culture and Survival Assay

Sympathetic neurons from superior cervical ganglia (SCG) of new-born rats (p4) are dissociated in dispase, plated at a density of $10^4$ cells/$cm^2$ in 48 well MTT plates coated with rat tail collagen, and cultured in Leibowitz medium containing 5% rat serum, 0.75 µg/mL NGF 7S (Boehringer Mannheim Corp., Indianapolis, Ind.) and arabinosine $10^5$M. Cell death is induced at day 4 after plating by exposing the culture to medium containing 10 µg/1 mL of anti NGF anti-body (Boehringer Mannheim Corp., Indianapolis, Ind.) and no NGF or arabinosine, in the presence or absence of sulfonamide inhibitors. 24 hours after cell death induction, determination of cell viability is performed by incubation of the culture for 1 hour, at 37° C. in 0.5 mg/mL of 3-(4,5-dimethylthiazol-2-yl) 2,5 diphenyl tetrazolium bromide (MTT). After incubation in MTT cells are resuspended in DMSO, transferred to a 96 MTT plate and cell viability is evaluated by measuring optical density at 590 nm.

The results of this assay with various test compounds demonstrate that compounds of Formula I are rescuing neurons from cells death (% neurons alive between 10 and 80)

Il-2 Release Assay:

Jurkat cells, a human T cell leukemia cell line (American Type Culture Collection # TIB 152) were cultured in RPMI 1640 medium (Gibco, BRL) supplemented with 10% of heatactivated FCS, Glutamine and Penstrep. The cell suspension in the medium is diluted to give $2.10^6$ cells/mL. The cells were plated ($2.10^5$ cells/well) on a 96-well plate containing different concentration of test compound (final concentration of compounds, 10, 3, 1, 0.3, 0.1 µM). This mixture is incubated 30 minutes at 37° C. in a humidified $CO_2$ atmosphere. Cells were then treated with 10 ul PMA+Ionomycine (0.1 µM and 1 µM final concentration) in all wells except negative control. In wells without compounds, 10 µl of RPMI 2% DMSO (=0.1% final) is added. Cells are incubated 24 hours at 37° C. and then the supernatant harvested (freeze at −20° C. if not used the same day) prior to performing IL-2 ELISA test on the supernatant.

IL-2 ELISA Assay:

IL-2 release into the medium by PMA+Iono-stimulated Jurkat cells, in presence or absence of test compounds is assayed by ELISA. Following the procedure described below Solutions Wash buffer: PBS-Tween 0.05%

Diluent: PBS-Tween 0.05%

Substrate Solution: Citric acid 0.1M/$Na_2HPO_4$ 0.1M

Stop solution: $H_2SO_4$ 20%

Matched Antibody Pairs/Standard:

From R&D Systems

Monoclonal anti-human IL-2 antibody (MAB602) (capture)

Biotinylated anti-human IL-2 antibody (BAF202) (detection)

Recombinant human IL-2 (202-IL-010) (standard)

Plate Preparation

Transfer 100 µl capture antibody diluted in PBS at 5 µg/mL into a 96 well ELISA plate and incubate overnight at room temperature.

Aspirate each well and wash 3 times with Wash buffer. After the last wash, damp the plate.

1. Saturate with 200 µl PBS-10% FCS. Incubate 1 hour at room temperature.

2. Repeat the wash step 2.

Assay Procedure

1. Add 100 µl of sample or standard (2000, 1000, 500, 250, 125, 62.5, 31.25 pg/mL) and incubate 2 hours at room temperature.

2. Wash 3 times.

3. Add 100 µl of biotinylated anti-human IL-2 at 12.5 ng/mL. Incubate 2 hours at room temperature.

4. Wash 3 times.

5. Add 100 µl streptavidin-HRP (Zymed #43-4323) at 1:10, 000. Incubate 30 minutes at room temperature.

6. Wash 3 times

7. Add 100 µl substrate solution (citric acid/$Na_2HPO_4$ (1:1)+$H_2O_2$ 1:2000+OPD). Incubate 20-30 minutes at room temperature.

8. Add 50 µl of stop solution to each well.

9. Determine optical density using a microtiter plate reader set to 450 nm with correction at 570 nm.

The result of this assay with various test compounds is summarized below:

| Example | % Inhibition of IL2 Production @ 3 uM |
|---------|---------------------------------------|
| 1       | >30                                   |
| 13      | >30                                   |
| 20      | >30                                   |
| 75      | >30                                   |
| 80      | >30                                   |

C-Jun Reporter Assay

Cell Culture

Hlr c-Jun HeLa cells are cultured in DMEM High Glc supplemented with 10% FCS (Sigma), 2 mM Glutamine (Gibco), P/S, Hygromycin b 100 µg/mL and G418 250 µg/mL Cell Culture Preparation Cell Banks The cells are stored frozen in cryotubes under liquid nitrogen, as 1.8 mL volumes of cell suspension in culture medium containing 10% dimethyl sulfoxide. Cells are kept in culture for no more than 20 passages.

Cell Culture Thawing

When necessary, frozen vials of cells are thawed rapidly at 37° C. in a water bath by gently swirling up to semi-complete thawing. Then the cell suspension are added to 10 mL of culture medium.

The cell suspension is then centrifuged for 5 minutes at 1200 rpm, the supernatant is removed and the cell pellet reconstituted in the medium and add to a 175 cm² flask containing 25 mL medium. The flasks are incubated at 37° C. in an atmosphere of 5% $CO_2$.

Cell Passage

The cells are serially subcultured (passaged) when 80% confluent monolayers have been obtained.

The medium of each flask is removed and the monolayer is washed with 10-15 mL of phosphate buffer solution (PBS).

Trypsin-EDTA solution is added to the cell monolayer, incubated at 37° C. and tapped gently at intervals to dislodge the cells. Complete detachment and disaggregation of the cell monolayer is confirmed by microscopy examination. The cells are then resuspended in 10 mL of complete medium and centrifuged for 5 minutes at 1200 rpm.

The supernatant are discarded, the cells are resuspended in culture medium and diluted 1/5 in 175 cm² flasks.

Day 0 Morning

Prepare Cells for Transfections

The cells from flasks of near-confluent cultures are detached and disaggregated by treatment with trypsin as described above.

The cells are resuspended in culture medium and counted.

The cell suspension are diluted with medium to give about 3.5×10⁶ cells/mL and 1 mL µl of cell suspension are put onto 210 cm culture dishes containing 9 mL of culture medium. The plates are incubated at 37° C. in a humidified atmosphere of 5% $CO_2$ in air Day 0 Evening Transfections Control: 0.2 µg pTK *Renilla*, 5.8%1 g pBluescript KS, 500 µl OPTIMEM (GIBCO), 18 µl Fugene 6

Induced: 0.1 µg pMEKK1, 0.2 µg pTK *Renilla*, 5.7 µg pBluescript KS, 500 µl OPTIMEM (GIBCO), 18 µl Fugene 630' RT The transfection mixture is added to the plated cells. The plates are incubated over night at 37° C. in a humidified atmosphere of 5% $CO_2$ in air Day 1

A 96 wells plate containing 100 µl of culture medium per well is prepared Negative control (vehicle): 2 µl of DMSO is added to the 100 µl (in triplicate). Compound: 2 µl of Hit compound stock dilution are added to the 100 µl (in triplicate). The transfected cells are trypsinised and ressuspend in 12 mL of culture medium. 100 µl of the dilution are added to each of the 96 wells plate.

The plate is incubated over night at 37° C. in a humidified atmosphere of 5% $CO_2$ in air Hit Compound Dilutions Hit compound stock concentrations are the following:
3, 1 and 0.1 mM in 100% DMSO.

Day 2

Test Procedure

Dual-Luciferase™ Reporter Assay System (Promega)

The medium is removed from the plate and the cells washed two times with 100 µl PBS Completely remove the rinse solution before applying PLB reagent. Dispense into each culture well 5 µl of 1X PLB. Place the culture plates on a rocking platform or orbital shaker with gentle rocking/shaking to ensure complete and even coverage of the cell monolayer with 1X PLB. Rock the culture plates at room temperature for 15 minutes. Transfer 20 µl of the lysate into a white opaque 96 wells plate. Read in a luminometer.

Inject 50 µl of Luciferase Assay Reagent II wait 5", read 10"

Inject 50 µl of Stop & Glo® Reagent wait 5", read 10"

Check RLU Luciferase/RLU *Renilla*\*1000

The result of this assay with various test compounds is summarized below:

| Example | % inhibition @ 10 uM |
|---------|----------------------|
| 1       | >20                  |
| 13      | >20                  |
| 20      | >20                  |
| 75      | >20                  |
| 80      | >20                  |

LPS Induced Endotoxin Shock in Mice

The ability of the JNK inhibitors described in formula I to significantly reduce the level of inflammatory cytokines induced by LPS challenge was assessed using the following protocol:

LPS (*S. abortus*-Galanos Lab-) was injected (200 µg/kg, i.v.) to Male C57BL/6 to induce endotoxin shock and compounds (0.1, 1, 10 mg/kg) or NaCl (200 uM) were injected intravenously (10 mL/kg) 15 min before the LPS challenge. Heparinized blood was obtained from the orbital sinus at different time points after the LPS challenge, and the blood was centrifuged at 9,000 rpm for 10 min at 4° C. to collect supernatant for the measurement of cytokines production by mouse ELISA kit such as IFNγ (Duoset R&D Ref. DY485).

The test compounds displayed considerable capability to reduce inflammatory related cytokines.

Global Ischemia in Gerbils

The ability of the JNK inhibitors described in formula I to protect cell death during a stroke event was assessed using the following protocol:

-1- METHOD

* Surgery
  Anesthesia: halothane or isoflurane (0.5-4%).
  Sheaving of the gorge and incision of the skin.
  The common carotid arteries (left and right) are freed from tissue.
  Occlusion of the arteries using Bulldog microclamps during 5 min.
  Disinfection of the surgery plan (Betadine®) and suture of the skin (Autoclip® ou Michel's hooks).
  Stabulation of the animals under heating lamp until awake.
  Stabulation of the animals in the animalry in individual cages.

* Sacrifice of the Animals
  7 days after ischemia (Decapitation or overdose of pentobarbital).
  Sampling of the brain.

Histological Parameters
  Freezing of the brain in isopentane (−20° C.)
  Slicing of the hippocampus using a cryo-microtome (20 μm).
  Staining with cresyl violet and/or TUNEL method
  Evaluation of the lesions (in CA1/CA2 subfields of the hippocampus)
    Gerhard & Boast score modified or
    Cell counting in the CA1/CA2

* Biochemical Parameters
  Microdissection of the cerebral structures
  Parameters determined: DNA fragmentation, lactate, calcium penetration.
  Analytical methods: ELISA, colorimetry, enzymology, radiometry.

-2- TREATMENT
  Administration of the test article or the vehicle: 15 min after reperfusion (5-10 min after the recovery of the anesthesia).
  Standard protocol
  50 animals: 5 groups of 10 (group A: control, groups B-D: test article at 3 doses and group E: reference compound (ketamine 3×120 mg/kg, ip or Orotic acid 3×300 mg/kg, ip).

The test compounds displayed considerable capability to protect from neuronal apoptosis during induced global ischemia.

The invention claimed is:

1. A sulfonyl hydrazide compound according to formula I

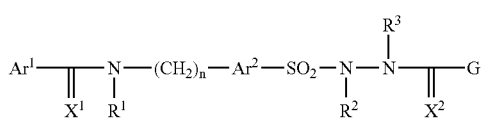

I geometrical isomers thereof, optically active enantiomers thereof, diastereomers thereof, racemates thereof, and/or pharmaceutically acceptable salts thereof, wherein $Ar^1$ and $Ar^2$ are independently from each other an unsubstituted or substituted aryl or heteroaryl group, $X^1$ and $X^2$ are independently from each other O or S;

$R^1$, $R^2$, $R^3$ are independently from each other hydrogen or a $C_1$-$C_6$-alkyl substituent or $R^1$ forms a substituted or unsubstituted 5-6-membered saturated or unsaturated ring with $Ar^1$;

or $R^2$ and $R^3$ form a substituted or unsubstituted 5-6-membered saturated or unsaturated ring;

n is an integer from 1 to 5;

G is an unsubstituted or substituted 4-8 membered heterocycle containing at least one heteroatom;

with the proviso that if $Ar^1$ is 4-chlorophenyl, $Ar^2$ is thienyl, $X^1$ and $X^2$ are O, $R^1$, $R^2$ and $R^3$ are H, n is 1, G is not one of the following:

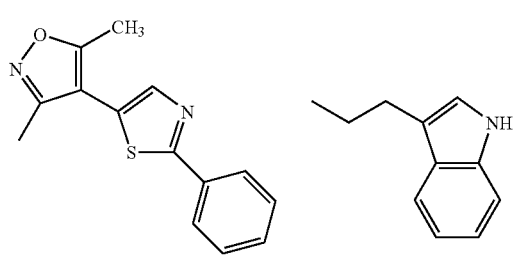

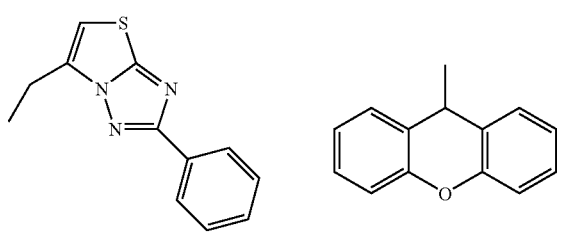

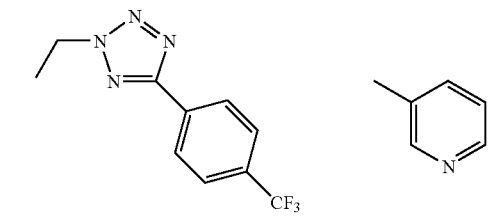

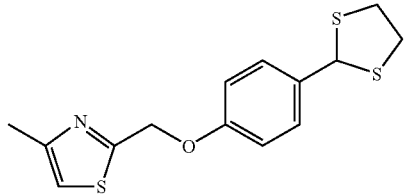

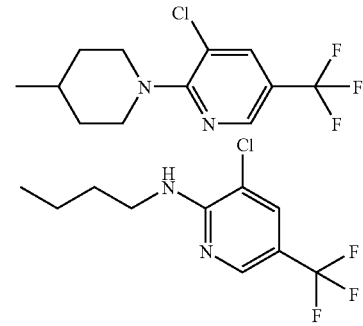

-continued

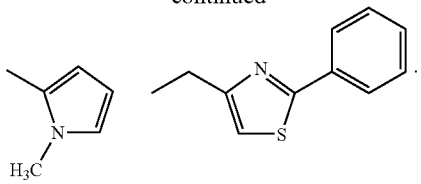

2. A sulfonyl hydrazide compound according to formula I

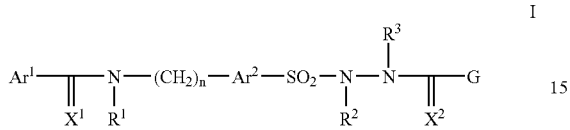

geometrical isomers thereof, optically active enantiomers thereof, diastereomers thereof, racemates thereof, and/or pharmaceutically acceptable salts thereof, wherein
$Ar^1$ and $Ar^2$ are independently from each other an unsubstituted or substituted aryl or heteroaryl group,
$X^1$ and $X^2$ are independently from each other O or S;
$R^1$, $R^2$, $R^3$ are independently from each other hydrogen or a $C_1$-$C_6$-alkyl substituent or $R^1$ forms a substituted or unsubstituted 5-6-membered saturated or unsaturated ring with $Ar^1$;
or $R^2$ and $R^3$ form a substituted or unsubstituted 5-6-membered saturated or unsaturated ring;
n is an integer from 0 to 5;
G is an unsubstituted or substituted 4-8 membered heterocycle containing at least one heteroatom.

3. A sulfonyl hydrazide compound according to formula I

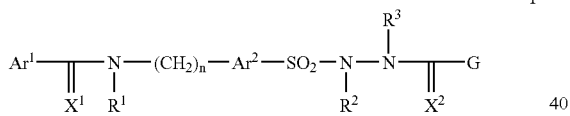

geometrical isomers thereof, optically active enantiomers thereof, diastereomers thereof, racemates thereof, and/or pharmaceutically acceptable salts thereof, wherein
$Ar^1$ and $Ar^2$ are independently from each other an unsubstituted or substituted aryl or heteroaryl group,
$X^1$ and $X^2$ are independently from each other O or S;
$R^1$, $R^2$, $R^3$ are independently from each other hydrogen or a $C_1$-$C_6$-alkyl substituent or $R^1$ forms a substituted or unsubstituted 5-6-membered saturated or unsaturated ring with $Ar^1$;
or $R^2$ and $R^3$ form a substituted or unsubstituted 5-6-membered saturated or unsaturated ring;
n is an integer from 0 to 5;
G is

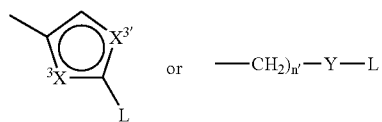

wherein, both $X^3$ and $X^{3'}$ are selected independently from each other from the group consisting of N, O, S or CHL';

Y is O, S or $NR^4$, whereby $R^4$ is H or an unsubstituted or substituted $C_1$-$C_6$-alkyl, an unsubstituted or substituted aryl or heteroaryl;
n' is an integer from 0 to 5,
L and L' are independently H, unsubstituted or substituted $C_1$-$C_6$-aliphatic alkyl, unsubstituted or substituted $C_2$-$C_6$-alkenyl, unsubstituted or substituted $C_2$-$C_6$-alkynyl, unsubstituted or substituted cyclic $C_4$-$C_8$-alkyl, optionally containing 1-3 heteroatoms and optionally fused with aryl or heteroaryl; or L is an unsubstituted or substituted aryl or heteroaryl, aryl-$C_1$-$C_6$-alkyl, heteroaryl-$C_1$-$C_6$-alkyl, —C(O)—$OR^5$, —C(O)—$R^5$, —C(O)—$NR^{5'}R^5$, —$NR^{5'}R^5$, —$NR^{5'}C(O)R^5$, —$NR^{5'}C(O)NR^{5'}R^5$, —$(SO)R^5$, —$(SO_2)R^5$, —$NSO_2R^5$, or —$SO_2NR^{5'}R^5$;
whereby, $R^5$ and $R^{5'}$ are substituents being independently H, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted aryl, unsubstituted or substituted heteroaryl, unsubstituted or substituted aryl-$C_1$-$C_6$-alkyl, unsubstituted or substituted heteroaryl-$C_1$-$C_6$-alkyl;
said aryl or heteroaryl groups being optionally substituted by unsubstituted or substituted $C_1$-$C_6$-alkyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, aminoacyl, aminocarbonyl, unsubstituted or substituted $C_1$-$C_6$-alkoxycarbonyl, aryl, carboxyl, cyano, halogen, hydroxy, nitro, sulfoxy, sulfonyl, $C_1$-$C_6$-thioalkoxy.

4. A sulfonyl hydrazide compound according to claim 1, wherein $Ar^1$ and/or $Ar^2$ are independently selected from the group consisting of phenyl, thienyl, furyl, pyridyl, pyrazolyl, pyrimidinyl, imidazolyl, naphthyl, quinolyl, optionally substituted by unsubstituted or substituted $C_1$-$C_6$-alkyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, acylamino, amino-carbonyl, unsubstituted or substituted $C_1$-$C_6$-alkoxycarbonyl, aryl, carboxyl, cyano, halogen, hydroxy, nitro, sulfoxy, sulfonyl, $C_1$-$C_6$-thioalkoxy.

5. A sulfonyl hydrazide compound according to formula I

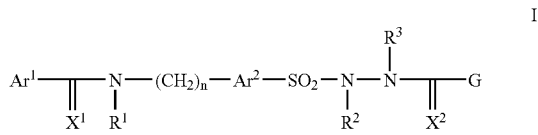

geometrical isomers thereof, optically active enantiomers thereof, diastereomers thereof, racemates thereof, and/or pharmaceutically acceptable salts thereof, wherein
$Ar^1$ is a substituted or unsubstituted phenyl, $X^1$ and $X^2$ are O, while $R^1$, $R^2$, $R^3$ are all hydrogen, n is 1, $Ar^2$ is thienyl, G is selected from

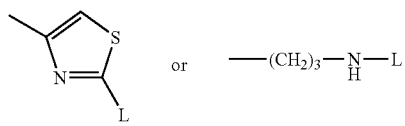

whereby L is H, unsubstituted or substituted $C_1$-$C_6$-aliphatic alkyl, unsubstituted or substituted $C_1$-$C_6$- alkenyl, unsubstituted or substituted $C_1$-$C_6$-alkynyl, unsubstituted or substituted cyclic $C_4$-$C_8$-alkyl, optionally containing 1-3 heteroatoms and optionally fused with aryl or heteroaryl; or L is an unsubstituted or substituted aryl or heteroaryl, aryl-$C_1$-$C_6$-alkyl, heteroaryl-$C_1$-C-alkyl, —C(O)—$OR^5$, —C(O)—$R^5$, —C(O)—$NR^{5'}R^5$, —$NR^{5'}R^5$, —$NR^{5'}C(O)R^5$, —$NR^{5'}C(O)NR^{5'}R^5$, —$(SO)R^5$, —$(SO_2)R^5$, —$NSO_2R^5$, or —$SO_2NR^{5'}R^5$.

6. A sulfonyl hydrazide compound according to formula I

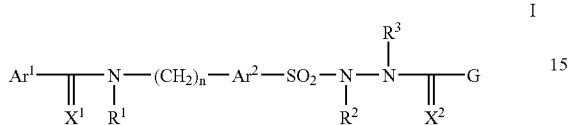

geometrical isomers thereof, optically active enantiomers thereof, diastereomers thereof, racemates thereof, and/or pharmaceutically acceptable salts thereof, wherein $Ar^1$ and $Ar^2$ are independently from each other an unsubstituted or substituted aryl or heteroaryl group, $X^1$ and $X^2$ are independently from each other O or S;

$R^1$, $R^2$, $R^3$ are independently from each other hydrogen or a $C_1$-$C_6$-alkyl substituent or $R^1$ forms a substituted or unsubstituted 5-6-membered saturated or unsaturated ring with $Ar^1$;

or $R^2$ and $R^3$ form a substituted or unsubstituted 5-6-membered saturated or unsaturated ring;

n is an integer from 0 to 5, and
G is

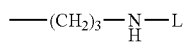

whereby L is H, unsubstituted or substituted $C_1$-$C_6$-aliphatic alkyl, unsubstituted or substituted $C_2$-$C_6$-alkenyl, unsubstituted or substituted $C_2$-$C_6$-alkynyl, unsubstituted or substituted cyclic $C_4$-$C_8$-alkyl, optionally containing 1-3 heteroatoms and optionally fused with aryl or heteroaryl; or L is an unsubstituted or substituted aryl or heteroaryl, aryl-$C_1$-$C_6$-alkyl, heteroaryl-$C_1$-$C_6$-alkyl, —C(O)—$OR^5$, —C(O)—$R^5$, —C(O)—$NR^{5'}R^5$, —$NR^{5'}R^5$, —$NR^{5'}C(O)R^5$, —$NR^{5'}C(O)NR^{5'}R^5$, —$(SO)R^5$, —$(SO_2)R^5$, —$NSO_2R^5$, or —$SO_2NR^{5'}R^5$.

7. A sulfonyl hydrazide compound according to claim 6, wherein L is a substituted or unsubstituted pyridyl group.

8. A sulfonyl hydrazide compound selected from the following group:

4-chloro-N-[(5-{[2-({2-[4-(1,3-dithiolan-2-yl)phenyl]-1,3-thiazol-4-yl}carbonyl)-hydrazino]sulfonyl}thien-2-yl)methyl]benzamide 4-chloro-N-{[5-({2-[(2-phenyl-1,3-thiazol-4-yl)carbonyl]hydrazino}sulfonyl)thien-2-yl]methyl}benzamide 4-chloro-N-{[5-({2-[(2-{[(4-chlorophenyl)sulfonyl]methyl}-1,3-thiazol-4-yl)carbonyl]hydrazino}sulfonyl)thien-2-yl]methyl}benzamide 4-chloro-N-{[5-({2-[(2-methyl-1,3-thiazol-4-yl)carbonyl]hydrazino}sulfonyl)thien-2-yl]methyl}benzamide 4-chloro-N-[(5-{[2-({2-[4-(1H-pyrrol-1-yl)phenyl]-1,3-thiazol-4-yl}carbonyl)-hydrazino]sulfonyl}thien-2-yl)methyl]benzamide 4-chloro-N-[(5-{[2-({2-[(4,5-dichloro-1H-imidazol-1-yl)methyl]-1,3-thiazol-4-yl}carbonyl)hydrazino]sulfonyl}thien-2-yl)methyl]benzamide 4-chloro-N-[(5-{[2-({2-[5-(trifluoromethyl)pyridin-2-yl]-1,3-thiazol-4-yl}carbonyl)hydrazino]sulfonyl}thien-2-yl)methyl]benzamide 4-chloro-N-[(5-{[2-({2-[3-chloro-5-(trifluoromethyl)pyridin-2-yl]-1,3-thiazol-4-yl}carbonyl)hydrazino]sulfonyl}thien-2-yl)methyl]benzamide 4-chloro-N-[(5-{[2-({2-[2-chloro-4-(trifluoromethyl)phenyl]-1,3-thiazol-4-yl}carbonyl)hydrazino]sulfonyl}thien-2-yl)methyl]benzamide 4-chloro-N-[(5-{[2-({2-[4-(trifluoromethyl)pyridin-3-yl]-1,3-thiazol-4-yl}-carbonyl)hydrazino]sulfonyl}thien-2-yl)methyl]benzamide 4-chloro-N-({5-[(2-{[2-(2,3-dichlorophenyl)-1,3-thiazol-4-yl]carbonyl}-hydrazino)sulfonyl]thien-2-yl}methyl)benzamide 4-chloro-N-{[5-({2-[(2-{[(2-furylmethyl)sulfonyl]methyl}-1,3-thiazol-4-yl)carbonyl]hydrazino}sulfonyl)thien-2-yl]methyl}benzamide 4-chloro-N-[(5-{[2-({2-[(2-chlorophenoxy)methyl]-1,3-thiazol-4-yl}carbonyl)-hydrazino]sulfonyl}thien-2-yl)methyl]benzamide 4-chloro-N-({5-[(2-{[2-(2,6-dichlorobenzyl)-1,3-thiazol-4-yl]carbonyl}hydrazino)-sulfonyl]thien-2-yl}methyl)benzamide N-[(5-{[2-({2-[4-(1,3-dithiolan-2-yl)phenyl]-1,3-thiazol-4-yl}carbonyl)hydrazino]-sulfonyl}thien-2-yl)methyl]-3-nitrobenzamide N-[(5-{[2-({2-[4-(1,3-dithiolan-2-yl)phenyl]-1,3-thiazol-4-yl}carbonyl)hydrazino]-sulfonyl}thien-2-yl)methyl]-3-methoxybenzamide N-[(5-{[2-({2-[4-(1,3-dithiolan-2-yl)phenyl]-1,3-thiazol-4-yl}carbonyl)hydrazino]-sulfonyl}thien-2-yl)methyl]-4-nitrobenzamide N'-(4-{[3-chloro-5-(trifluoromethyl)pyridin-2-yl]amino}butanoyl)-5-[(1,3-dioxo-1,3-dihydro-2H-isoindol-2-yl)methyl]thiophene-2-sulfonohydrazide N-[(5-{[2-(4-{[3-chloro-5-(trifluoromethyl)pyridin-2-yl]amino}butanoyl)-hydrazino]sulfonyl}thien-2-yl)methyl]-4-nitrobenzamide N-[(5-{[2-(4-{[3-chloro-5-(trifluoromethyl)pyridin-2-yl]amino}butanoyl)-hydrazino]sulfonyl}thien-2-yl)methyl]-3-hydroxybenzamide N-[(5-{[2-(4-{[3-chloro-5-(trifluoromethyl)pyridin-2-yl]amino}butanoyl)-hydrazino]sulfonyl}thien-2-yl)methyl]-2-hydroxybenzamide N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2-furamide N-[(5-{[2-(4-{[3-chloro-5-(trifluoromethyl)pyridin-2-yl]amino}butanoyl)-hydrazino]sulfonyl}thien-2-yl)methyl]-2-thien-2-ylacetamide N-[(5-{[2-(4-{[3-chloro-5-(trifluoromethyl)pyridin-2-yl]amino}butanoyl)-hydrazino]sulfonyl}thien-2-yl)methyl]-1-naphthamide N-[(5-{[2-(4-{[3-chloro-5-(trifluoromethyl)pyridin-2-yl]amino}butanoyl)-hydrazino]sulfonyl}thien-2-yl)methyl]-2-naphthamide N-[(5-{[2-(4-{[3-chloro-5-(trifluoromethyl)pyridin-2-yl]amino}butanoyl)-hydrazino]sulfonyl}thien-2-yl)methyl]-4-methylbenzamide N-[(5-{[2-(4-{[3-chloro-5-(trifluoromethyl)pyridin-2-yl]amino}butanoyl)-hydrazino]sulfonyl}thien-2-yl)methyl]-4-ethylbenzamide 4-tert-butyl-N-[(5-{[2-(4-{[3-chloro-5-(trifluoromethyl)pyridin-2-yl]amino}-butanoyl)hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2-fluorobenzamide N-[(5-{[2-(4-{[3-chloro-5-(trifluoromethyl)pyridin-2-yl]amino}butanoyl)-hydrazino]sulfonyl}thien-2-yl)methyl]-3-fluorobenzamide N-[(5-{[2-(4-{[3-chloro-5-(trifluoromethyl)pyridin-2-yl]amino}butanoyl)-hydrazino]sulfonyl}thien-2-yl)methyl]-4-fluorobenzamide N-[(5-{[2-(4-{[3-chloro-5-(trifluoromethyl)pyridin-2-yl]amino}butanoyl)-hydrazino]sulfonyl}thien-2-yl)methyl]-2,6-difluorobenzamide N-[(5-{[2-(4-{[3-chloro-5-(trifluoromethyl)pyridin-2-yl]amino}butanoyl)-hydrazino]sulfonyl}thien-2-yl)methyl]-3,5-difluorobenzamide 2-chloro-N-[(5-{[2-(4-{[3-chloro-5-(trifluoromethyl)pyridin-2-yl]amino}-butanoyl)hydrazino]sulfonyl}thien-2-yl)methyl]benzamide 3-chloro-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-4-iodobenzamide 2,6-dichloro-N-[(5-{[2-(4-{[3-chloro-5-(trifluoromethyl)pyridin-2-yl]amino}-butanoyl)hydrazino]sulfonyl}thien-2-yl)methyl]benzamide 3,5-dichloro-N-[(5-{[2-(4-{[3-chloro-5-(trifluoromethyl)pyridin-2-yl]amino}-butanoyl)hydrazino]sulfonyl}thien-2-yl)methyl]benzamide 2-bromo-N-[(5-{[2-(4-{[3-chloro-5-(trifluoromethyl)pyridin-2-yl]amino}-butanoyl)hydrazino]sulfonyl}thien-2-yl)methyl]benzamide 3-bromo-N-[(5-{[2-(4-{[3-chloro-5-(trifluoromethyl)pyridin-2-yl]amino}-butanoyl)hydrazino]sulfonyl}thien-2-yl)methyl]benzamide 4-bromo-N-[(5-{[2-(4-{[3-chloro-5-(trifluoromethyl)pyridin-2-yl]amino}-butanoyl)hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2-iodobenzamide N-[(5-{[2-(4-{[3-chloro-5-(trifluoromethyl)pyridin-2-yl]amino}butanoyl)-hydrazino]sulfonyl}thien-2-yl)methyl]-3-nitrobenzamide N-[(5-{[2-(4-{[3-chloro-5-(trifluoromethyl)pyridin-2-yl]amino}butanoyl)-hydrazino]sulfonyl}thien-2-yl)methyl]-2-nitrobenzamide N-[(5-{[2-(4-{[3-chloro-5-(trifluoromethyl)pyridin-2-yl]amino}butanoyl)-hydrazino]sulfonyl}thien-2-yl)methyl]-4-(dimethylamino)benzamide N-[(5-{[2-(4-{[3-chloro-5-(trifluoromethyl)pyridin-2-yl]amino}butanoyl)-hydrazino]sulfonyl}thien-2-yl)methyl]-3-methoxybenzamide N-[(5-{[2-(4-{[3-chloro-5-(trifluoromethyl)pyridin-2-yl]amino}butanoyl)-hydrazino]sulfonyl}thien-2-yl)methyl]-2-methoxybenzamide N-[(5-{[2-(4-{[3-chloro-5-(trifluoromethyl)pyridin-2-yl]amino}butanoyl)-hydrazino]sulfonyl}thien-2-yl)methyl]-4-methoxybenzamide N-[(5-{[2-(4-{[3-chloro-5-(trifluoromethyl)pyridin-2-yl]amino}butanoyl)-hydrazino]sulfonyl}thien-2-yl)methyl]-2,6-dimethoxybenzamide N-[(5-{[2-(4-{[3-chloro-5-(trifluoromethyl)pyridin-2-yl]amino}butanoyl)-hydrazino]sulfonyl}thien-2-yl)methyl]-3,5-dimethoxybenzamide N-[(5-{[2-(4-{[3-chloro-5-(trifluoromethyl)pyridin-2-yl]amino}butanoyl)-hydrazino]sulfonyl}thien-2-yl)methyl]-2-(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]-3-(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]-4-(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]-3,5-bis(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]nicotinamide N-[(5-{[2-(4-{[3-chloro-5-(trifluoromethyl)pyridin-2-yl]amino}butanoyl)-hydrazino]sulfonyl}thien-2-yl)methyl]isonicotinamide 4-amino-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-4-hydroxybenzamide N-[(5-{[2-(4-{[3-chloro-5-(trifluoromethyl)pyridin-2-yl]amino}butanoyl)-hydrazino]sulfonyl}thien-2-yl)methyl]-3,4-dihydroxybenzamide 3,4-diamino-N-[(5-{[2-(4-{[3-chloro-5-(trifluoromethyl)pyridin-2-yl]amino}-butanoyl)hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]pyridine-2-carboxamide N-[(5-{[2-(4-{[3-chloro-5-(trifluoromethyl)pyridin-2-yl]amino}butanoyl)-hydrazino]sulfonyl}thien-2-yl)methyl]-6-hydroxypyridine-2-carboxamide 6-amino-N-[(5-{[2-(4-{[3-chloro-5-(trifluoromethyl)pyridin-2-yl]amino}butanoyl)-hydrazino]sulfonyl}thien-2-yl)methyl]nicotinamide N-[(5-{[2-(4-{[3-chloro-5-(trifluoromethyl)pyridin-2-yl]amino}butanoyl)-hydrazino]sulfonyl}thien-2-yl)methyl]-2-sulfanylnicotinamide N-[(5-{[2-(4-{[3-chloro-5-(trifluoromethyl)pyridin-2-yl]amino}butanoyl)-hydrazino]sulfonyl}thien-2-yl)methyl]-6-sulfanylnicotinamide N-[(5-{[2-(4-{[3-chloro-5-(trifluoromethyl)pyridin-2-yl]amino}butanoyl)-hydrazino]sulfonyl}thien-2-yl)methyl]-2,6-dihydroxyisonicotinamide N-[(5-{[2-(4-{[3-chloro-5-(trifluoromethyl)pyridin-2-yl]amino}butanoyl)-hydrazino]sulfonyl}thien-2-yl)methyl]-5-nitro-1H-pyrazole-3-carboxamide N-[(5-{[2-(4-{[3-chloro-5-(trifluoromethyl)pyridin-2-yl]amino}butanoyl)-hydrazino]sulfonyl}thien-2-yl)methyl]-2-hydroxy-6-methoxybenzamide N-[(5-{[2-(4-{[3-chloro-5-(trifluoromethyl)pyridin-2-yl]amino}butanoyl)-hydrazino]sulfonyl}thien-2-yl)methyl]-8-hydroxyquinoline-7-carboxamide 2-amino-N-[(5-{[2-(4-{[3-chloro-5-(trifluoromethyl)pyridin-2-yl]amino}-butanoyl)hydrazino]sulfonyl}thien-2-yl)methyl]nicotinamide N-[(5-{[2-(4-{[3-chloro-5-(trifluoromethyl)pyridin-2-yl]amino}butanoyl)-hydrazino]sulfonyl}thien-2-yl)methyl]-4-fluoro-3-nitrobenzamide 2-amino-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2,3,4-trihydroxybenzamide N-[(5-{[2-(4-{[3-chloro-5-(trifluoromethyl)pyridin-2-yl]amino}butanoyl)-hydrazino]sulfonyl}thien-2-yl)methyl]-2-oxo-1,2-dihydropyridine-3-carboxamide N-[(5-{[2-(4-{[3-chloro-5-(trifluoromethyl)pyridin-2-yl]amino}butanoyl)-hydrazino]sulfonyl}thien-2-yl)methyl]-2,4-dihydroxybenzamide N-[(5-{[2-(4-{[3-chloro-5-(trifluoromethyl)pyridin-2-yl]amino}butanoyl)-hydrazino]sulfonyl}thien-2-yl)methyl]-5-hydroxypyridine-2-carboxamide N-[(5-{[2-(4-{[3-chloro-5-(trifluoromethyl)pyridin-2-yl]amino}butanoyl)-hydrazino]sulfonyl}thien-2-yl)methyl]-2,4-dioxo-1,2,3,4-tetrahydropyrimidine-5-carboxamide N-[(5-{[2-(4-{[3-chloro-5-(trifluoromethyl)pyridin-2-yl]amino}butanoyl)-hydrazino]sulfonyl}thien-2-yl)methyl]-1H-imidazole-4-carboxamide 4-chloro-N-(4-{[2-(4-{[3-chloro-5-(trifluoromethyl)pyridin-2-yl]amino}-butanoyl)hydrazino]sulfonyl}benzyl)benzamide 4-chloro-N-(2-{[2-(4-{[3-chloro-5-(trifluoromethyl)pyridin-2-yl]amino}-butanoyl)hydrazino]sulfonyl}phenyl)benzamide 4-chloro-N-(3-{[2-(4-{[3-chloro-5-(trifluoromethyl)pyridin-2-yl]amino}-butanoyl)hydrazino]sulfonyl}phenyl)benzamide N-(4-{[2-(4-{[3-chloro-5-(trifluoromethyl)pyridin-2-yl]amino}butanoyl)-hydrazino]sulfonyl}benzyl)-3-nitrobenzamide 4-chloro-N-(3-{[2-(4-{[3-chloro-5-(trifluoromethyl)pyridin-2-yl]amino}-butanoyl)hydrazino]sulfonyl}benzyl)benzamide N-(3-{[2-(4-{[3-chloro-5-(trifluoromethyl)pyridin-2-yl]amino}butanoyl)-hydrazino]sulfonyl}benzyl)benzamide N-(3-{[2-(4-{[3-chloro-5-(trifluoromethyl)pyridin-2-yl]amino}butanoyl)-hydrazino]sulfonyl}benzyl)-2-hydroxybenzamide N-(3-{[2-(4-{[3-chloro-5-(trifluoromethyl)pyridin-2-yl]amino}butanoyl)-hydrazino]sulfonyl}benzyl)-3-nitrobenzamide.

9. A sulfonamide compound according to claim 8, which is selected from the group consisting of 4-chloro-N-[(5-{[2-({2-[4-(1,3-dithiolan-2-yl)phenyl]-1,3-thiazol-4-yl}carbonyl)hydrazino]sulfonyl}thien-2-yl)methyl]benzamide 4-chloro-N-[(5-{[2-({2-[(2-chlorophenoxy)methyl]-1,3-thiazol-4-yl}carbonyl)hydrazino]sulfonyl}thien-2-yl)methyl]benzamide N-[(5-{[2-(4-{[3-chloro-5-(trifluoromethyl)pyridin-2-yl]amino}butanoyl)hydrazino]sulfonyl}thien-2-yl)methyl]-2-hydroxybenzamide N-[(5-{[2-(4-{[3-chloro-5-(trifluoromethyl)pyridin-2-yl]amino}butanoyl)hydrazino]sulfonyl}thien-2-yl)methyl]-2-oxo-1,2-dihydropyridine-3-carboxamide 4-chloro-N-(4-{[2-(4-{[3-chloro-5-(trifluoromethyl)pyridin-2-yl]amino}butanoyl)hydrazino]sulfonyl}benzyl)benzamide.

10. A pharmaceutical composition containing at least one sulfonyl hydrazide compound according to claim 1 and a pharmaceutically acceptable carrier, diluent or excipient thereof.

11. A process for the preparation of the sulfonyl hydrazide compound according to claim 1 comprising a) preparing a sulfonyl compound V

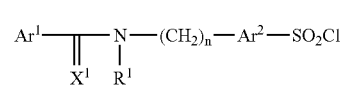

b) and reacting it with the hydrazide compound VIII

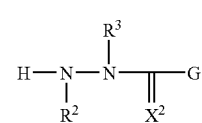

whereby the substituents $Ar^1, Ar^2, R^1, R^2, R^3, X^1, X^2$ and G are as defined in claim 1.

12. A sulfonyl hydrazide compound according to claim 2, wherein G is

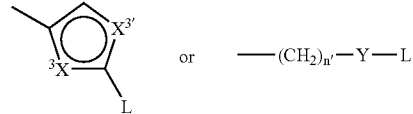

wherein, both $X^3$ and $X^{3'}$ are selected independently from each other from the group consisting of N, O, S or CHL';

Y is O, S or $NR^4$, whereby $R^4$ is H or an unsubstituted or substituted $C_1$-$C_6$-alkyl, an unsubstituted or substituted aryl or heteroaryl;

n' is an integer from 0 to 5;

L and L' are independently selected from the group consisting of H, unsubstituted or substituted $C_1$-$C_6$-aliphatic alkyl, unsubstituted or substituted $C_2$-$C_6$-alkenyl, unsubstituted or substituted $C_2$-$C_6$-alkynyl, unsubstituted or substituted cyclic $C_4$-$C_8$-alkyl, optionally containing 1-3 heteroatoms and optionally fused with aryl or heteroaryl; or L is an unsubstituted or substituted aryl or heteroaryl, aryl-$C_1$-$C_6$-alkyl, heteroaryl-$C_1$-$C_6$-alkyl, —C(O)—$OR^5$, —C(O)—$R^5$, —C(O)—$NR^{5'}R^5$, —$NR^{5'}R^5$, $NR^{5'}C(O)R^5$, —$NR^{5'}C(O)NR^{5'}R^5$, —(SO)$R^5$, —(SO$_2$)$R^5$, —$NSO_2R^5$, —$SO_2NR^{5'}R^5$;

whereby, $R^5$ and $R^{5'}$ are substituents being independently selected from the group consisting of H, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted aryl, unsubstituted or substituted heteroaryl, unsubstituted or substituted aryl-$C_1$-$C_6$-alkyl, unsubstituted or substituted heteroaryl-$C_1$-$C_6$-alkyl;

said aryl or heteroaryl groups being optionally substituted by unsubstituted or substituted $C_1$-$C_6$-alkyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, aminoacyl, aminocarbonyl, unsubstituted or substituted $C_1$-$C_6$-alkoxycarbonyl, aryl, carboxyl, cyano, halogen, hydroxy, nitro, sulfoxy, sulfonyl, $C_1$-$C_6$-thioalkoxy.

13. A sulfonyl hydrazide compound according to claim 2, wherein $Ar^1$ and/or $Ar^2$ are independently selected from the group consisting of phenyl, thienyl, furyl, pyridyl, pyrazolyl, pyrimidinyl, imidazolyl, naphthyl, quinolyl, optionally substituted by unsubstituted or substituted $C_1$-$C_6$-alkyl, unsubstituted or substituted $C_1$-$C_6$-alkoxy, unsubstituted or substituted $C_2$-$C_6$-alkenyl, unsubstituted or substituted $C_2$-$C_6$-alkynyl, amino, acylamino, amino-carbonyl, unsubstituted or substituted $C_1$-$C_6$-alkoxycarbonyl, aryl, carboxyl, cyano, halogen, hydroxy, nitro, sulfoxy, sulfonyl, $C_1$-$C_6$-thioalkoxy.

14. A sulfonyl hydrazide compound according to claim 2, wherein $Ar^1$ is a substituted or unsubstituted phenyl, $X^1$ and $X^2$ are O, while $R^1$, $R^2$, $R^3$ are all hydrogen, n is 1, $Ar^2$ is thienyl, G is selected from

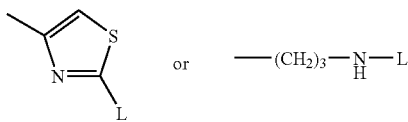

whereby L is H, unsubstituted or substituted $C_1$-$C_6$-aliphatic alkyl, unsubstituted or substituted $C_2$-$C_6$-alkenyl, unsubstituted or substituted $C_2$-$C_6$-alkynyl, unsubstituted or substituted cyclic $C_{4-8}$-alkyl, optionally containing 1-3 heteroatoms and optionally fused with aryl or heteroaryl; or L is an unsubstituted or substituted aryl or heteroaryl, aryl-$C_1$-$C_6$-alkyl, heteroaryl-$C_1$-$C_6$-alkyl, —C(O)—OR$^5$, —C(O)—R$^5$, —C(O)—NR$^{5'R5}$, —NR$^{5'}R^5$, —NR$^{5'}$C(O)R$^5$, —NR$^{5'}$C(O)NR$^{5'}R^5$, —(SO)R$^5$, —(SO$_2$)R$^5$: —NSO$_2$R$^5$, or —SO$_2$NR$^{5'}R^5$.

15. A sulfonyl hydrazide compound according to claim 2, wherein G is

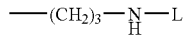

whereby L is H, unsubstituted or substituted $C_1$-$C_6$-aliphatic alkyl, unsubstituted or substituted $C_2$-$C_6$-alkenyl, unsubstituted or substituted $C_2$-$C_6$-alkynyl, unsubstituted or substituted cyclic $C_4$-$C_8$-alkyl, optionally containing 1-3 heteroatoms and optionally fused with aryl or heteroaryl; or L is an unsubstituted or substituted aryl or heteroaryl, aryl-$C_1$-$C_6$-alkyl, heteroaryl-$C_1$-$C_6$-alkyl, —C(O)—OR$^5$, —C(O)—R$^5$, —C(O)—NR$^{5'}R^5$, —NR$^{5'}R^5$, —NR$^{5'}$C(O)R$^5$, —NR$^{5'}$C(O)NR$^{5'}R^5$, —(SO)R$^5$, —SO$_2$)R$^5$, —NSO$_2$R$^5$, —SO$_2$NR$^{5'}R^5$.

16. A sulfonyl hydrazide compound according to claim 15, wherein L is a substituted or unsubstituted pyridyl group.

17. A sulfonyl hydrazide compound according to claim 2 selected from the following group:

4-chloro-N-[(5-{[2-({2-[4-(1,3-dithiolan-2-yl)phenyl]-1,3-thiazol-4-yl}carbonyl)-hydrazino]sulfonyl}thien-2-yl)methyl]benzamide 4-chloro-N-{[5-({2-[(2-phenyl-1,3-thiazol-4-yl)carbonyl]hydrazino}sulfonyl)thien-2-yl]methyl}benzamide 4-chloro-N-{[5-({2-[(2-{[(4-chlorophenyl)sulfonyl]methyl}-1,3-thiazol-4-yl)-carbonyl]hydrazino}sulfonyl)thien-2-yl]methyl}benzamide 4-chloro-N-{[5-({2-[(2-methyl-1,3-thiazol-4-yl)carbonyl]hydrazino}sulfonyl)thien-2-yl]methyl}benzamide 4-chloro-N-[(5-{[2-({2-[4-(1H-pyrrol-1-yl)phenyl]-1,3-thiazol-4-yl}carbonyl)-hydrazino]sulfonyl}thien-2-yl)methyl]benzamide 4-chloro-N-[(5-{[2-({2-[(4,5-dichloro-1H-imidazol-1-yl)methyl]-1,3-thiazol-4-yl}carbonyl)hydrazino]sulfonyl}thien-2-yl)methyl]benzamide 4-chloro-N-[(5-{[2-({2-[5-(trifluoromethyl)pyridin-2-yl]-1,3-thiazol-4-yl}carbonyl)hydrazino]sulfonyl}thien-2-yl)methyl]benzamide 4-chloro-N-[(5-{[2-({2-[3-chloro-5-(trifluoromethyl)pyridin-2-yl]-1,3-thiazol-4-yl}carbonyl)hydrazino]sulfonyl}thien-2-yl)methyl]benzamide 4-chloro-N-[(5-{[2-({2-[2-chloro-4-(trifluoromethyl)phenyl]-1,3-thiazol-4-yl}carbonyl)hydrazino]sulfonyl}thien-2-yl)methyl]benzamide 4-chloro-N-[(5-{[2-({2-[4-(trifluoromethyl)pyridin-3-yl]-1,3-thiazol-4-yl}-carbonyl)hydrazino]sulfonyl}thien-2-yl)methyl]benzamide 4-chloro-N-({5-[(2-{[2-(2,3-dichlorophenyl)-1,3-thiazol-4-yl]carbonyl}-hydrazino)sulfonyl]thien-2-yl}methyl)benzamide 4-chloro-N-{[5-({2-[(2-{[(2-furylmethyl)sulfonyl]methyl}-1,3-thiazol-4-yl)carbonyl]hydrazino}sulfonyl)thien-2-yl]methyl}benzamide 4-chloro-N-[(5-{[2-({2-[(2-chlorophenoxy)methyl]-1,3-thiazol-4-yl}carbonyl)-hydrazino]sulfonyl}thien-2-yl)methyl]benzamide 4-chloro-N-({5-[(2-{[2-(2,6-dichlorobenzyl)-1,3-thiazol-4-yl]carbonyl}hydrazino)-sulfonyl]thien-2-yl}methyl)benzamide N-[(5-{[2-({2-[4-(1,3-dithiolan-2-yl)phenyl]-1,3-thiazol-4-yl}carbonyl)hydrazino]-sulfonyl}thien-2-yl)methyl]-3-nitrobenzamide N-[(5-{[2-({2-[4-(1,3-dithiolan-2-yl)phenyl]-1,3-thiazol-4-yl}carbonyl)hydrazino]-sulfonyl}thien-2-yl)methyl]-3-methoxybenzamide N-[(5-{[2-({2-[4-(1,3-dithiolan-2-yl)phenyl]-1,3-thiazol-4-yl}carbonyl)hydrazino]-sulfonyl}thien-2-yl)methyl]-4-nitrobenzamide N'-(4-{[3-chloro-5-(trifluoromethyl)pyridin-2-yl]amino}butanoyl)-5-[(1,3-dioxo-1,3-dihydro-2H-isoindol-2-yl)methyl]thiophene-2-sulfonohydrazide N-[(5-{[2-(4-{[3-chloro-5-(trifluoromethyl)pyridin-2-yl]amino}butanoyl)-hydrazino]sulfonyl}thien-2-yl)methyl]-4-nitrobenzamide N-[(5-{[2-(4-{[3-chloro-5-(trifluoromethyl)pyridin-2-yl]amino}butanoyl)-hydrazino]sulfonyl}thien-2-yl)methyl]-3-hydroxybenzamide N-[(5-{[2-(4-{[3-chloro-5-(trifluoromethyl)pyridin-2-yl]amino}butanoyl)-hydrazino]sulfonyl}thien-2-yl)methyl]-2-hydroxybenzamide N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2-furamide N-[(5-{[2-(4-{[3-chloro-5-(trifluoromethyl)pyridin-2-yl]amino}butanoyl)-hydrazino]sulfonyl}thien-2-yl)methyl]-2-thien-2-ylacetamide N-[(5-{[2-(4-{[3-chloro-5-(trifluoromethyl)pyridin-2-yl]amino}butanoyl)-hydrazino]sulfonyl}thien-2-yl)methyl]-1-naphthamide N-[(5-{[2-(4-{[3-chloro-5-(trifluoromethyl)pyridin-2-yl]amino}butanoyl)-hydrazino]sulfonyl}thien-2-yl)methyl]-2-naphthamide N-[(5-{[2-(4-{[3-chloro-5-(trifluoromethyl)pyridin-2-yl]amino}butanoyl)-hydrazino]sulfonyl}thien-2-yl)methyl]-4-methylbenzamide N-[(5-{[2-(4-{[3-chloro-5-(trifluoromethyl)pyridin-2-yl]amino}butanoyl)-hydrazino]sulfonyl}thien-2-yl)methyl]-4-ethylbenzamide 4-tert-butyl-N-[(5-{[2-(4-{[3-chloro-5-(trifluoromethyl)pyridin-2-yl]amino}-butanoyl)hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2-fluorobenzamide N-[(5-{[2-(4-{[3-chloro-5-(trifluoromethyl)pyridin-2-yl]amino}butanoyl)-hydrazino]sulfonyl}thien-2-yl)methyl]-3-fluorobenzamide N-[(5-{[2-(4-{[3-chloro-5-(trifluoromethyl)pyridin-2-yl]amino}butanoyl)-hydrazino]sulfonyl}thien-2-yl)methyl]-4-fluorobenzamide N-[(5-{[2-(4-{[3-chloro-5-(trifluoromethyl)pyridin-2-yl]amino}butanoyl)-hydrazino]sulfonyl}thien-2-yl)methyl]-2,6-difluorobenzamide N-[(5-{[2-(4-{[3-chloro-5-(trifluoromethyl)pyridin-2-yl]amino}butanoyl)-hydrazino]sulfonyl}thien-2-yl)methyl]-3,5-difluorobenzamide 2-chloro-N-[(5-{[2-(4-{[3-chloro-5-(trifluoromethyl)pyridin-2-yl]amino}-butanoyl)hydrazino]sulfonyl}thien-2-yl)methyl]benzamide 3-chloro-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-4-iodobenzamide 2,6-dichloro-N-[(5-{[2-(4-{[3-chloro-5-(trifluoromethyl)pyridin-2-yl]amino}-butanoyl)hydrazino]sulfonyl}thien-2-yl)methyl]benzamide 3,5-dichloro-N-[(5-{[2-(4-{[3-chloro-5-(trifluoromethyl)pyridin-2-yl]amino}-butanoyl)hydrazino]sulfonyl}thien-2-yl)methyl]benzamide 2-bromo-N-[(5-{[2-(4-{[3-chloro-5-(trifluoromethyl)pyridin-2-yl]amino}-butanoyl)hydrazino]sulfonyl}thien-2-yl)methyl]benzamide 3-bromo-N-[(5-{[2-(4-{[3-chloro-5-(trifluoromethyl)pyridin-2-yl]amino}-butanoyl)hydrazino]sulfonyl}thien-2-yl)methyl]benzamide 4-bromo-N-[(5-{[2-(4-{[3-chloro-5-(trifluoromethyl)pyridin-2-yl]amino}-butanoyl)hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2-iodobenzamide N-[(5-{[2-(4-{[3-chloro-5-(trifluoromethyl)pyridin-2-yl]amino}butanoyl)-hydrazino]sulfonyl}thien-2-yl)methyl]-3-nitrobenzamide N-[(5-{[2-(4-{[3-chloro-5-(trifluoromethyl)pyridin-2-yl]amino}butanoyl)-hydrazino]sulfonyl}thien-2-yl)methyl]-2-nitrobenzamide N-[(5-{[2-(4-{[3-chloro-5-(trifluoromethyl)pyridin-2-yl]amino}butanoyl)-hydrazino]sulfonyl}thien-2-yl)methyl]-4-(dimethylamino)benzamide N-[(5-{[2-(4-{[3-chloro-5-(trifluoromethyl)pyridin-2-yl]amino}butanoyl)-hydrazino]sulfonyl}thien-2-yl)methyl]-3-methoxybenzamide N-[(5-{[2-(4-{[3-chloro-5-(trifluoromethyl)pyridin-2-yl]amino}butanoyl)-hydrazino]sulfonyl}thien-2-yl)methyl]-2-methoxybenzamide N-[(5-{[2-(4-{[3-chloro-5-(trifluoromethyl)pyridin-2-yl]amino}butanoyl)-hydrazino]sulfonyl}thien-2-yl)methyl]-4-methoxybenzamide N-[(5-{[2-(4-{[3-chloro-5-(trifluoromethyl)pyridin-2-yl]amino}butanoyl)-hydrazino]sulfonyl}thien-2-yl)methyl]-2,6-dimethoxybenzamide N-[(5-{[2-(4-{[3-chloro-5-(trifluoromethyl)pyridin-2-yl]amino}butanoyl)-hydrazino]sulfonyl}thien-2-yl)methyl]-3,5-dimethoxybenzamide N-[(5-{[2-(4-{[3-chloro-5-(trifluoromethyl)pyridin-2-yl]amino}butanoyl)-hydrazino]sulfonyl}thien-2-yl)methyl]-2-(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]-3-(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]-4-(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]-3,5-bis(trifluoromethyl)benzamide N-[(5-{[2-(4-{[3-chloro-5-(trifluoromethyl)pyridin-2-yl]amino}butanoyl)-hydrazino]sulfonyl}thien-2-yl)methyl]nicotinamide N-[(5-{[2-(4-{[3-chloro-5-(trifluoromethyl)pyridin-2-yl]amino}butanoyl)-hydrazino]sulfonyl}thien-2-yl)methyl]isonicotinamide 4-amino-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-4-hydroxybenzamide N-[(5-{[2-(4-{[3-chloro-5-(trifluoromethyl)pyridin-2-yl]amino}butanoyl)-hydrazino]sulfonyl}thien-2-yl)methyl]-3,4-dihydroxybenzamide 3,4-diamino-N-[(5-{[2-(4-{[3-chloro-5-(trifluoromethyl)pyridin-2-yl]amino}-butanoyl)hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]pyridine-2-carboxamide N-[(5-{[2-(4-{[3-chloro-5-(trifluoromethyl)pyridin-2-yl]amino}butanoyl)-hydrazino]sulfonyl}thien-2-yl)methyl]-6-hydroxypyridine-2-carboxamide 6-amino-N-[(5-{[2-(4-{[3-chloro-5-(trifluoromethyl)pyridin-2-yl]amino}butanoyl)-hydrazino]sulfonyl}thien-2-yl)methyl]nicotinamide N-[(5-{[2-(4-{[3-chloro-5-(trifluoromethyl)pyridin-2-yl]amino}butanoyl)-hydrazino]sulfonyl}thien-2-yl)methyl]-2-sulfanylnicotinamide N-[(5-{[2-(4-{[3-chloro-5-(trifluoromethyl)pyridin-2-yl]amino}butanoyl)-hydrazino]sulfonyl}thien-2-yl)methyl]-6-sulfanylnicotinamide N-[(5-{[2-(4-{[3-chloro-5-(trifluoromethyl)pyridin-2-yl]amino}butanoyl)-hydrazino]sulfonyl}thien-2-yl)methyl]-2,6-dihydroxyisonicotinamide N-[(5-{[2-(4-{[3-chloro-5-(trifluoromethyl)pyridin-2-yl]amino}butanoyl)-hydrazino]sulfonyl}thien-2-yl)methyl]-5-nitro-1H-pyrazole-3-carboxamide N-[(5-{[2-(4-{[3-chloro-5-(trifluoromethyl)pyridin-2-yl]amino}butanoyl)-hydrazino]sulfonyl}thien-2-yl)methyl]-2-hydroxy-6-methoxybenzamide N-[(5-{[2-(4-{[3-chloro-5-(trifluoromethyl)pyridin-2-yl]amino}butanoyl)-hydrazino]sulfonyl}thien-2-yl)methyl]-8-hydroxyquinoline-7-carboxamide 2-amino-N-[(5-{[2-(4-{[3-chloro-5-(trifluoromethyl)pyridin-2-yl]amino}-butanoyl)hydrazino]sulfonyl}thien-2-yl)methyl]nicotinamide N-[(5-{[2-(4-{[3-chloro-5-(trifluoromethyl)pyridin-2-yl]amino}butanoyl)-hydrazino]sulfonyl}thien-2-yl)methyl]-4-fluoro-3-nitrobenzamide 2-amino-N-[(5-{[2-(4-{[3-chloro-5-(trifluoromethyl)pyridin-2-yl]amino}butanoyl)-hydrazino]sulfonyl}thien-2-yl)methyl]benzamide N-[(5-{[2-(4-{[3-chloro-5-(trifluoromethyl)pyridin-2-yl]amino}butanoyl)-hydrazino]sulfonyl}thien-2-yl)methyl]-2,3,4-trihydroxybenzamide N-[(5-{[2-(4-{[3-chloro-5-(trifluoromethyl)pyridin-2-yl]amino}butanoyl)-hydrazino]sulfonyl}thien-2-yl)methyl]-2-oxo-1,2-dihydropyridine-3-carboxamide N-[(5-{[2-(4-{[3-chloro-5-(trifluoromethyl)pyridin-2-yl]amino}butanoyl)-hydrazino]sulfonyl}thien-2-yl)methyl]-2,4-dihydroxybenzamide N-[(5-{[2-(4-{[3-chloro-5-(trifluoromethyl)pyridin-2-yl]amino}butanoyl)-hydrazino]sulfonyl}thien-2-yl)methyl]-5-hydroxypyridine-2-carboxamide N-[(5-{[2-(4-{[3-chloro-5-(trifluoromethyl)pyridin-2-yl]amino}butanoyl)-hydrazino]sulfonyl}thien-2-yl)methyl]-2,4-dioxo-1,2,3,4-tetrahydropyrimidine-5-carboxamide N-[(5-{[2-(4-{[3-chloro-5-(trifluoromethyl)pyridin-2-yl]amino}butanoyl)-hydrazino]sulfonyl}thien-2-yl)methyl]-1H-imidazole-4-carboxamide 4-chloro-N-(4-{[2-(4-{[3-chloro-5-(trifluoromethyl)pyridin-2-yl]amino}-butanoyl)hydrazino]sulfonyl}benzyl)benzamide 4-chloro-N-(2-{[2-(4-{[3-chloro-5-(trifluoromethyl)pyridin-2-yl]amino}-butanoyl)hydrazino]sulfonyl}phenyl)benzamide 4-chloro-N-(3-{[2-(4-{[3-chloro-5-(trifluoromethyl)pyridin-2-yl]amino}-butanoyl)hydrazino]sulfonyl}phenyl)benzamide N-(4-{[2-(4-{[3-chloro-5-(trifluoromethyl)pyridin-2-yl]amino}butanoyl)-hydrazino]sulfonyl}benzyl)-3-nitrobenzamide 4-chloro-N-(3-{[2-(4-{[3-chloro-5-(trifluoromethyl)pyridin-2-yl]amino}-butanoyl)hydrazino]sulfonyl}benzyl)benzamide N-(3-{[2-(4-{[3-chloro-5-(trifluoromethyl)pyridin-2-yl]amino}butanoyl)-hydrazino]sulfonyl}benzyl)benzamide N-(3-{[2-(4-{[3-chloro-5-(trifluoromethyl)pyridin-2-yl]amino}butanoyl)-hydrazino]sulfonyl}benzyl)-2-hydroxybenzamide N-(3-{[2-(4-{[3-chloro-5-(trifluoromethyl)pyridin-2-yl]amino}butanoyl)-hydrazino]sulfonyl}benzyl)-3-nitrobenzamide.

18. A sulfonamide compound according to claim 17, which is selected from the group consisting of 4-chloro-N-[(5-{[2-({2-[4-(1,3-dithiolan-2-yl)phenyl]-1,3-thiazol-4-yl}carbonyl)hydrazino]sulfonyl}thien-2-yl)methyl]benzamide 4-chloro-N-[(5-{[2-({2-[(2-chlorophenoxy)methyl]-1,3-thiazol-4-yl}carbonyl)hydrazino]sulfonyl}thien-2-yl)methyl]benzamide N-[(5-{[2-(4-{[3-chloro-5-(trifluoromethyl)pyridin-2-yl]amino}butanoyl)hydrazino]sulfonyl}thien-2-yl)methyl]-2-hydroxybenzamide N-[(5-{[2-(4-{[3-chloro-5-(trifluoromethyl)pyridin-2-yl]amino}butanoyl)hydrazino]sulfonyl}thien-2-yl)methyl]-2-oxo-1,2-dihydropyridine-3-carboxamide 4-chloro-N-(4-{[2-(4-{[3-chloro-5-(trifluoromethyl)pyridin-2-yl]amino}butanoyl)hydrazino]sulfonyl}benzyl)benzamide.

19. A pharmaceutical composition containing at least one sulfonyl hydrazide compound according to claim 2 and a pharmaceutically acceptable carrier, diluent or excipient thereof.

20. A process for the preparation of the sulfonyl hydrazide compound according to claim 2 comprising c) preparing a sulfonyl compound V $$Ar^1 \underset{X^1}{\overset{\phantom{X}}{=}}\!\!\!\underset{R^1}{N}\!\!-\!(CH_2)_n\!-\!Ar^2\!-\!SO_2Cl \qquad V$$

d) and reacting it with the hydrazide compound VIII $$H-\underset{R^2}{N}-\underset{\phantom{R}}{\overset{R^3}{N}}\underset{X^2}{\overset{\phantom{X}}{=}}G \qquad VIII$$

whereby the substituents $Ar^1$, $Ar^2$, $R^1$, $R^2$, $R_3$, $X^1$, $X^2$ and G are as defined in claim 2.

21. A sulfonyl hydrazide compound according to claim 3, wherein n' is an integer from 1-3.

22. A sulfonyl hydrazide compound according to claim 3, wherein n' is 3.

23. A sulfonyl hydrazide compound according to claim 5, wherein $Ar^1$ is 4-chlorophenyl.

24. A sulfonyl hydrazide compound according to claim 12, wherein n' is an integer from 1-3.

25. A sulfonyl hydrazide compound according to claim 12, wherein n' is 3.

26. A sulfonyl hydrazide compound according to claim 14, wherein $Ar^1$ is 4-chlorophenyl.

27. A sulfonyl hydrazide compound according to claim 6, wherein L is a substituted or unsubstituted pyridyl group.

28. A sulfonyl hydrazide compound according to claim 15, wherein L is a substituted or unsubstituted pyridyl group.

29. A pharmaceutical composition containing at least one sulfonyl hydrazide compound according to claim 3 and a pharmaceutically acceptable carrier, diluent or excipient thereof.

30. A pharmaceutical composition containing at least one sulfonyl hydrazide compound according to claim 5 and a pharmaceutically acceptable carrier, diluent or excipient thereof.

31. A pharmaceutical composition containing at least one sulfonyl hydrazide compound according to claim 6 and a pharmaceutically acceptable carrier, diluent or excipient thereof.

32. A pharmaceutical composition containing at least one sulfonyl hydrazide compound according to claim 8 and a pharmaceutically acceptable carrier, diluent or excipient thereof.

33. The sulfonyl hydrazide compound of claim 1, wherein n is an integer from 1 to 3.

* * * * *

UNITED STATES PATENT AND TRADEMARK OFFICE
CERTIFICATE OF CORRECTION

| | | |
|---|---|---|
| PATENT NO. | : 7,432,286 B1 | Page 1 of 1 |
| APPLICATION NO. | : 10/088074 | |
| DATED | : October 7, 2008 | |
| INVENTOR(S) | : Arkinstall et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1289 days.

Signed and Sealed this
First Day of November, 2011

David J. Kappos
*Director of the United States Patent and Trademark Office*